US006673937B2

(12) United States Patent
Lazo et al.

(10) Patent No.: US 6,673,937 B2
(45) Date of Patent: Jan. 6, 2004

(54) SYNTHESES AND METHODS OF USE OF NEW ANTIMITOTIC AGENTS

(75) Inventors: John S. Lazo, Pittsburgh, PA (US); Peter Wipf, Pittsburgh, PA (US); Billy W. Day, Pittsburgh, PA (US)

(73) Assignee: The University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/910,195

(22) Filed: Jul. 19, 2001

(65) Prior Publication Data

US 2002/0049221 A1 Apr. 25, 2002

Related U.S. Application Data

(60) Provisional application No. 60/219,282, filed on Jul. 19, 2000.

(51) Int. Cl.$^7$ ............... C07D 405/00; C07D 325/00; C07D 317/72

(52) U.S. Cl. ............... 546/282.7; 549/336; 549/337

(58) Field of Search ............... 549/336, 337; 546/282.7

(56) References Cited

U.S. PATENT DOCUMENTS 5,789,604 A  *  8/1998  Pearce et al. ............... 549/336

OTHER PUBLICATIONS

Weber et al., The Preussomerins: Novel Antifungal Metabolites from the Coprophilous Fungus *Preussia isomera* Cain, J. Org. Chem. 1991, 56, 4355–4360, American Chemical Society.
Talapatra et al, (−)–Regiolone, An α–Tetralone from Juglans Regia:Structure, Stereochemistry and Conformation, Phytochemistry, vol. 27, No. 12, pp. 3929–3932, 1988, Pergamon Press, Great Britain.
Singh et al., Preussomerins and Deoxypreussomerins: Novel Inhibitors of Ras Farnesyl–Protein Transferase, J. Org. Chem. 1994, 59, 6296–6302.
Krohn et al., New Palmarumycins $CP_{4a}$ and $CP_5$ from *Coniothyrium palmarum*:Structure Elucidation, Crystal Structure Analysis and Determination of the Absolute Configuration by CD Calculations, Tetrahedron, vol. 53, No. 9, pp. 3101–3110, 1997.
Bode et al., Biosynthesis of Cladospirone Bisepoxide, A Member of the Spirobisnaphthalene Family, The Journal of Antibiotics, vol. 53, No. 2, Feb. 2000, pp. 153–157. Germany.
Krohn et al., Generation of the Palmarumycin Spiroacetal Framework by Oxidative Cyclization of an Open Chain Metabolite from *Coniothyrium palmarum*, Liebigs Ann./Recueil 1997, 2531–2534, Wiley–VCH Verlag GmbH, Weinheim, Germany.
Ragot et al., Syntheses of Palmarumycin $CP_1$ and $CP_2$ CJ–12,371 and Novel Analogues, Tetrahedron Letters 39 (1998) 4921–4924, Elsevier Science Ltd., Pergamon, Great Britain.
Verdier–Pinard et al., Structure–Activity Analysis of the Interaction of Curacin A. the Potent Colchicine Site Antimitotic Agent, with Tubulin and Effects of Analogs on the Growth of MCF–7 Breast Cancer Cells, Molecular Pharmacology, 53:62–76 (1998).
Yu et al., UCN–01 Abrogates $G_2$ Arrest through a Cdc2–dependent Pathway That Is Associated with Inactivation of the Wee1Hu Kinase and Activation of the Cdc25C Phosphatase, The Journal of Biological Chemistry, vol. 273, No. 50, Issue of Dec. 1998.
Thiergardt et al., Cladospirone Bisepoxide: Definite Structure Assignment Including Absolute Configuration and Selective Chemical Transformations, Tetrahedron vol. 51, No. 3, pp. 733–742, 1995, Elsevier Science Ltd., Pergamon, Great Britain.
Chu et al., Sch 50673 and Sch 50676, Two Novel Antitumor Fungal Metabolites, vol. 48, No. 4, pp. 329–331, The Journal of Antiboiotics, Apr. 1995.
Chu et al., Two New Phospholipase D Inhibitors, SCH 49211 and SCH 49212, Produced by the Fungus *Nattrassia mangiferae*, Biorganic & Medicinal Chemistry Letters. vol. 4. No. 12. pp. 1539–1542. 1994. Elsevier Science Ltd., Pergamon, Great.
Chu et al., Structure of Sch 49209: A Novel Antitumor Agent from the Fungus *Nattrassia mangiferae*, J. Org. Chem. 1994, 59, 1222–1223, American Chemical Society.
McDonald et al., Spiroxins, DNA Cleaving Antitumor Antibiotics from a Marine–Derived Fungus, Tetrahedron Letters 40 (1999) 2489–2492, Pergamon, Elsevier Science Ltd.
Newhall et al., Synthesis of 8–Hydroxy–2–keto–5–methoxy–4a–methyl–2,3,4,4a,9, 10–hexahydrophenanthrene, vol. 77, pp. 5646–5652, 1955, J. Am. Chem. Soc.
WIPF et al., Formal Total Synthesis of (+)–Diepoxin σ, J. Org. Chem 2000, 65, 6319–6337, American Chemical Society.
Osada et al., Screening of Cell Cycle Inhibitors from Microbial Metabolites by a Bioassay Using a Mouse cdc2 Mutant Cell Line, tsFT210, Bioorganic & Medicinal Chemistry, vol. 5, No. 1, pp. 193–203, 1997 Elsevier Science Ltd., Pergamon, Great.

(List continued on next page.)

*Primary Examiner*—Alan L. Rotman
*Assistant Examiner*—Raymond Covington
(74) *Attorney, Agent, or Firm*—Thorp Reed & Armstrong, LLP

(57) ABSTRACT

Oxidative cyclization of bis-naphthyl ethers allows concise total syntheses of palmarumycin $CP_1$ and deoxypreussomerin A in 8-9 steps and 15–35% overall yield from 5-hydroxy-8-methoxy-1-tetralone. A small library of palmarumycin analogs was created. Biological evaluation of these naphthoquinone spiroketals against MCF-7 and MDA-MB-231 human breast cancer cells revealed several low-micromolar growth inhibitors. A number of the analogs inhibit the thioredoxin—thioredoxin reductase system.

2 Claims, 17 Drawing Sheets

OTHER PUBLICATIONS

Haldar et al., Inactivation of Bcl–2 by phosphorylation, Proc. Natl. Acad. Sci. USA, vol. 92, pp. 4507–4511, 1995, Medical Sciences.

Vogt et al., Disruption of Insulin–Like Growth Factor–1 Signaling and Down–Regulation of Cdc2 by SC–ααδ9, Novel Small Molecule Antisignaling Agent Identified in a Targeted Array Library, JPET 287:806–813, 1998, The American Society for Pharmacology and.

Pines, Four–dimensional control of the cell cycle, Nature Cell Biology, vol. 1, Jul. 1999, ppE73–E79.

Wipf et al., Total Synthesis of Palmarumycin CP1 and (±)–Deoxypreussomerin A, J. Org. Chem 1998, 63, 3530–3531, University of Pittsburgh, Pittsburgh, Pennsylvania.

Schlingmann et al., Diepoxins, Novel Fungal Metabolites with Antibiotic Activity, Tetrahedron Letters, vol. 34, No. 45, pp. 7225–7228, 1993, Pergamon Press Ltd., Great Britain.

Krohn et al., Palmarumycins C1–C16 from Coniothyrium sp.: Isolation, Structure Elucidation, and Biological Activity, Liebigs Ann. Chem. 1994, 1099–1108, VCH Verlagsgesellschaft mbH, Weinheim, Germany.

Rice et al., A Targeted Library of Small–Molecule, Tyrosine, and Dual–Specificity Phosphatase Inhibitors Derived from a Rational Core Design and Random Side Chain Variation, Biochemistry 1997, 36, 15965–15974, University of Pittsburgh, Pittsburgh, PA.

Powis et al., Thioredoxin redox control of cell growth and death and the effects of inhibitors, Chemico–Biological Interactions 111–112, 1998, 23–34, University of Arizona, Tucson, AZ and University of Regina, Saskathewan, CA.

Kunkel et al., Cell line–directed screening assay for inhibitors of thioredoxin reductase signaling as potential anti–cancer drugs, Anti–Cancer Drug Design, 1997, 12, 659–670, Oxford University Press.

Wipf et al., Total Synthesis of the Antimitotic Marine Natural Product (+)–Curacin A, J. Org. Chem. 1996, 61, 6556–6562, University of Pittsburgh, Pittsburgh, PA.

Th'ng, et al. The FT210 Cell Line Is A Mouse G2 Phase Mutant with a Temperature–Sensitive CDC2 Gene Product, Cell, vol. 63, 313–324, Oct., 1990, Cell Press, www-.cell.com.

Pines, Four–dimensional control of the cell cycle, Nature Cell Biology, vol. 1, Jul. 1999, www.cellbio.nature.com, Cambridge, U.K.

Hunter et al., Cyclins and Cancer II: Cyclin D and CDK Inhibitors Come of Age, Cell, vol. 79, 573–582, 1994, Cell Press.

Sakemi et al., CJ–12,371 and CJ–12,372, Two Novel DNA Gyrase Inhibitors Fermentation, Isolation, Structural Elucidation and Biological Acitivites, The Journal of Antibiotics, vol. 48, No. 2, Pfizer Inc., Groton, CT.

Schlingmann, et al., Absolute Stereochemistry of the Diepoxins, Tetrahedron, vol. 52, No. 2, pp. 435–446, Pergamon, Elsevier Science Ltd. 1995, Great Britain.

Soman, et al., Sporovexins A–C and a New Preussomerin Analog: Antibacterial and Antifungal Metabolites from the Coprophilous Fungus *Sporormiella vexans*, J. Nat. Prod. 1999, 62, 659–661, Amer. Chem. Society and Amer. Society of Pharmacognosy.

Ragot et al., The synthesis of 1,8–dihydroxynaphthalene–derived natural products: palmarumycin CP1, palmarumycin CP2, palmarumycin C11, CJ–12,371, deoxypreussomerin A and novel analogues, Perkin 1, 1999, Paper 9/010761, Glasgow.

Barrett et al., Total Syntheses of palmarumycins CP1 and CP2 and CJ–12,371: novel spiro–ketal fungal metabolites, Chem. Commun, 1998, 809–810,.

Wipf et al., Long–Range Electrostatic Effects in Synthesis: Dipole–Controlled Nucleophilic Addition to a Naphthoquinone Acetal in Model Studies toward Diepoxin σ, Angew.Chem. Int. Ed. Engl. 1997. 36, No. 7. 764–767, VCH VerlagsgesellschaftmbH.

Wipf et al., Total Synthesis of the Spiroketal Naphthoquinone (±)–Diepoxin σ, J. Org. Chem. 1999, 64, 1092–1093, American Chemical Society.

Chi et al., Total Syntheses of (±)–Preussomerins G and I, Org. Lett., vol. 1, No. 1, 1999, 3–5, American Chemical Society.

Graybill et al., The Metalation of 1–Methoxynapththalene with n–Butyllithium, 1966, 1221–1225.

Osborne, Steriod hormone receptors in breast cancer management, Breast Cancer Research and Treatment 51: 227–238, 1998, Kluwer Academic Publishers, The Netherlands.

Oblong, Purification of Human Thioredoxin Reductase: Properties and Characterizaion by Absorption and Circular Dichroism Spectroscopy, Biochemistry 1993, 32, 7271–7277, American Chemical Society.

Gasdaska, The predicted amino acid sequence of human thioredoxin is identical to that of the autocrine growth factor human adult T–cell derived factor (ADF): thioredoxin mRNA is elevated in some humar tumors, Biochimica et Biophysica Acta 1218 (1994) 292–296, Elsevier Science B.V.

Hamel et al., Separation of Active Tubulin and Microtubule–Associated Proteins by Ultracentrifugation and Isolation of a Component Causing the Formation of Microtubule Bundles. Biochemistry 1984. 23. 4173–4184. American Chemical Society.

Tamura et al., Dual G1 and G2/M phase inhibition by SC–ααδ9, a combinatorially derived Cdc25 phosphatase inhibitor, Oncogene (1999) 18, 6989–6995, Stockton Press.

Tamura et al., Cdc25 Inhibition and Cell Cycle Arrest by a Synthetic Thioalkyl Vitamin K Analogue[1]Cancer, Research 60, 1317–1325, 2000.

Weber et al., Structure of Preussomerin A: An Unusual New Antifungal Metabolite fromthe Coprophilous Fungus *Preussia isomera*, J. Am. Chem. Soc. 1990, 112, 6718–6719.

Mayer, et al., Small Molecule Inhibitor of Mitotic Spidle Bipolarity Identified in a Phenotype–Based Screen, Science, vol. 286, 1999 971–974.

Williams Jr., et al., Thioredoxin reductase, Minireview, Eur. J. Biochem. 267, 6110–6117 (2000) FEBS 2000.

Becker, et al., Thioredoxin reductase as a pathophysiological factor and drug target, Minireview, Eur. J. Biochem. 267, 6118–6125 (2000) FEBS 2000.

Vogt, et al., Antitumor Imidazolyl Disulfide IV–2 Causes Irreversible $G_2$/M Cell Cycle Arrest without Hyperphosphorylation of Cycl–Dependent Kinase Cdk1, The Journal of Pharmacology and Experimental Therapeutics, vol. 294, No. 3, 1070–1075, 2000.

Arner et al., Physiological functions of thioredoxin and thioredoxin reductase, Minireview, Eur. J. Biochem. 267, 6102–6109 (2000) FEBS 2000.

Foster, et al. Pharmacological Rescue of Mutant p53 Conformation and Function, Science, vol. 286, 2507–2510, 1999.

Chu et al., SCH 53823 and SCH 53825, Novel Fungal Metabolites with Phospholipase D Inhibitory Activity, Bioorganic & Medicinal Chemistry Letters, vol. 6, No. 5, pp. 579–584, 1996, Elsevier Science Ltd, Pergamon, Great Britain.

* cited by examiner

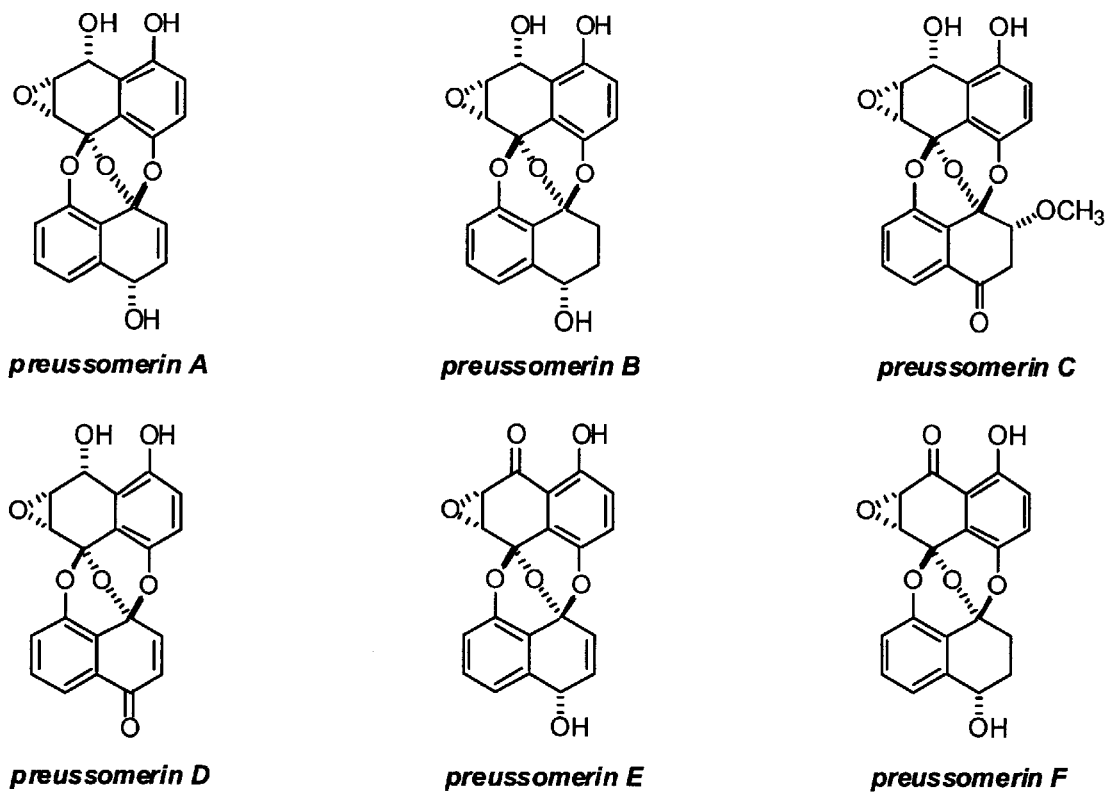
Figure 1
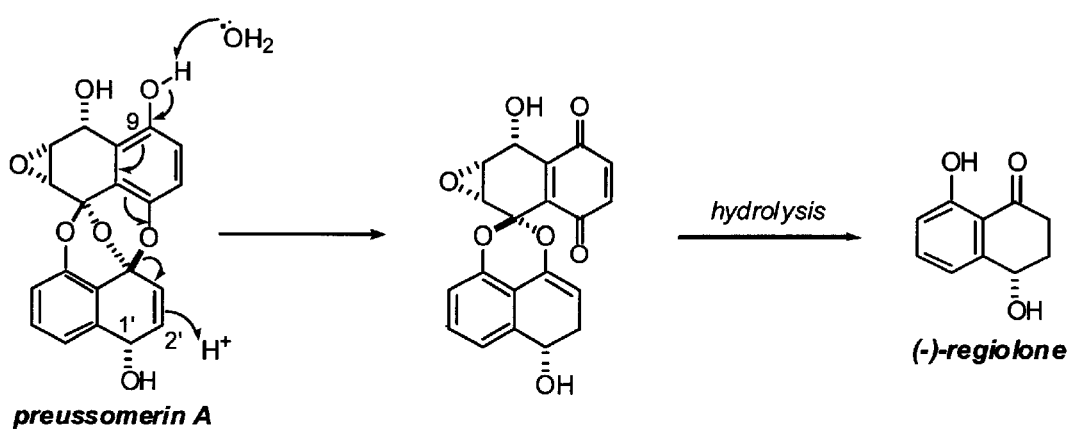
Figure 2. Acidic degradation of preussomerin A

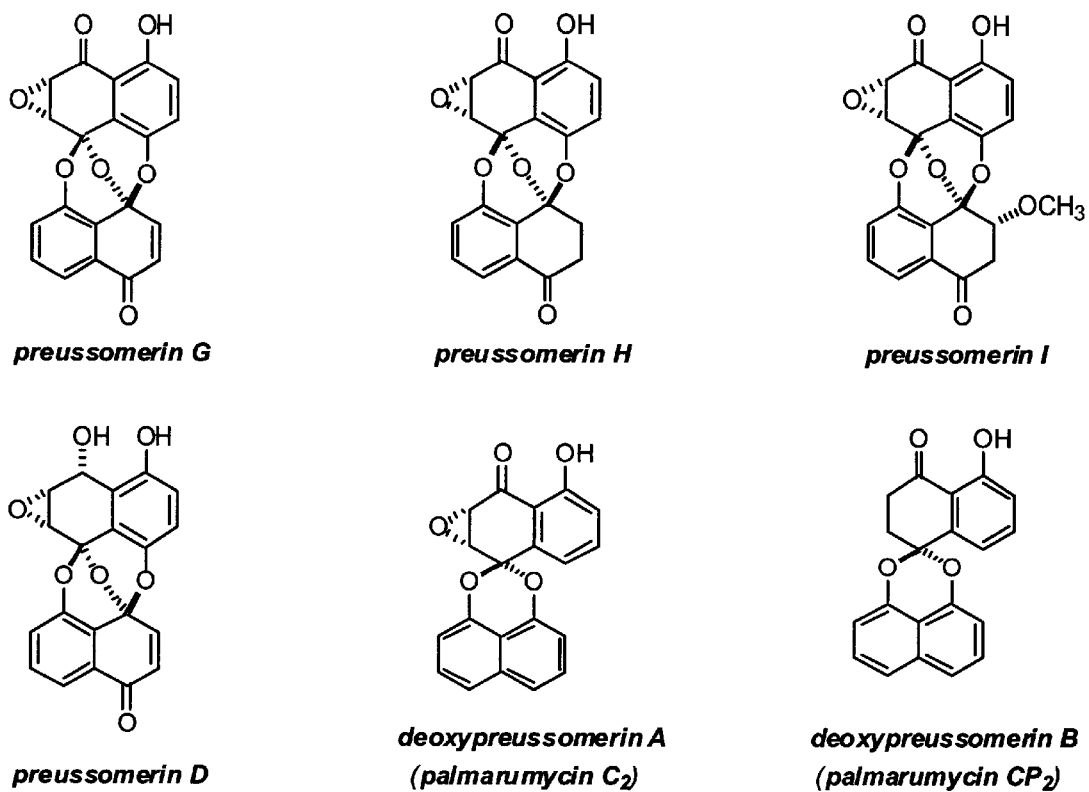
Figure 3. Preussomerins and deoxypreussomerins isolated from a coelomycetes fungus
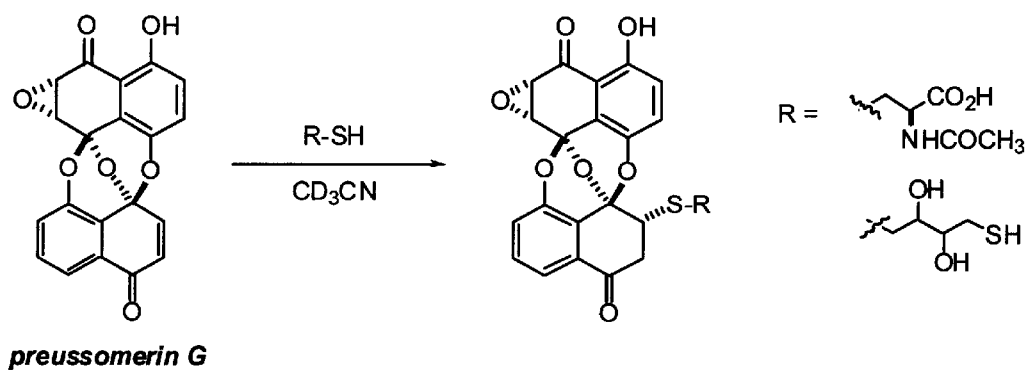
Figure 4

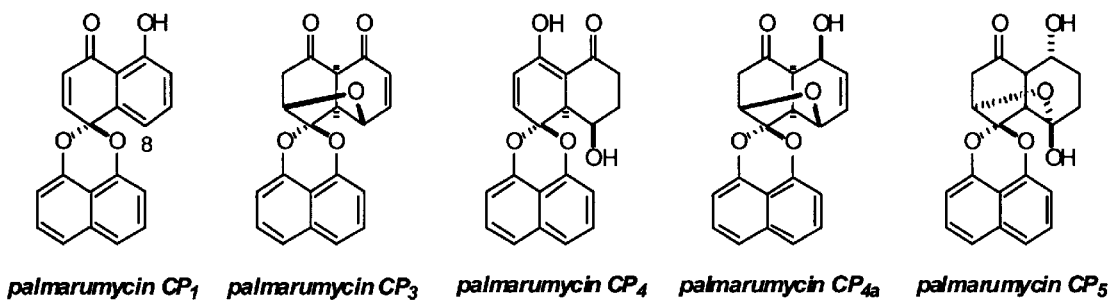
Figure 5 - Palmarumycins from *Coniothyrium palmarium*
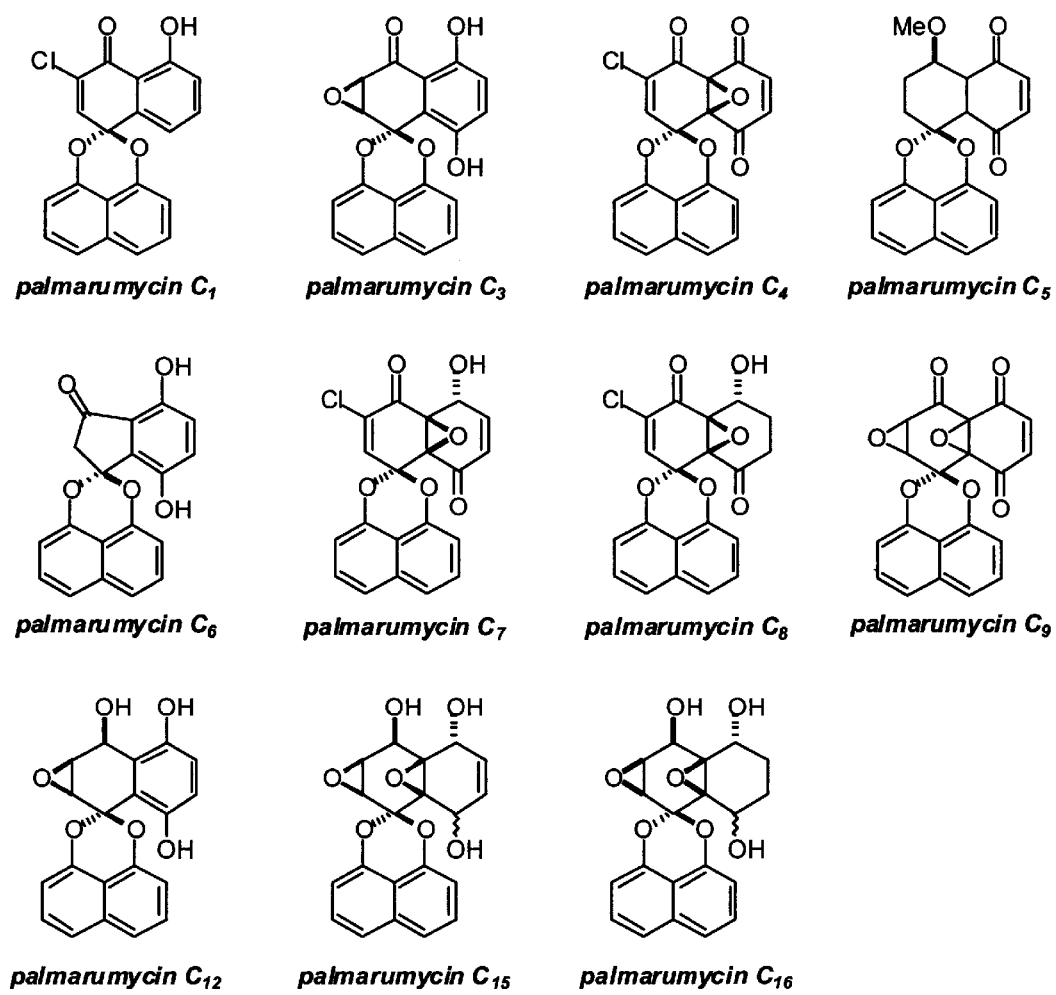
Figure 6 - Palmarumycins from an unidentified *Coniothyrium* species

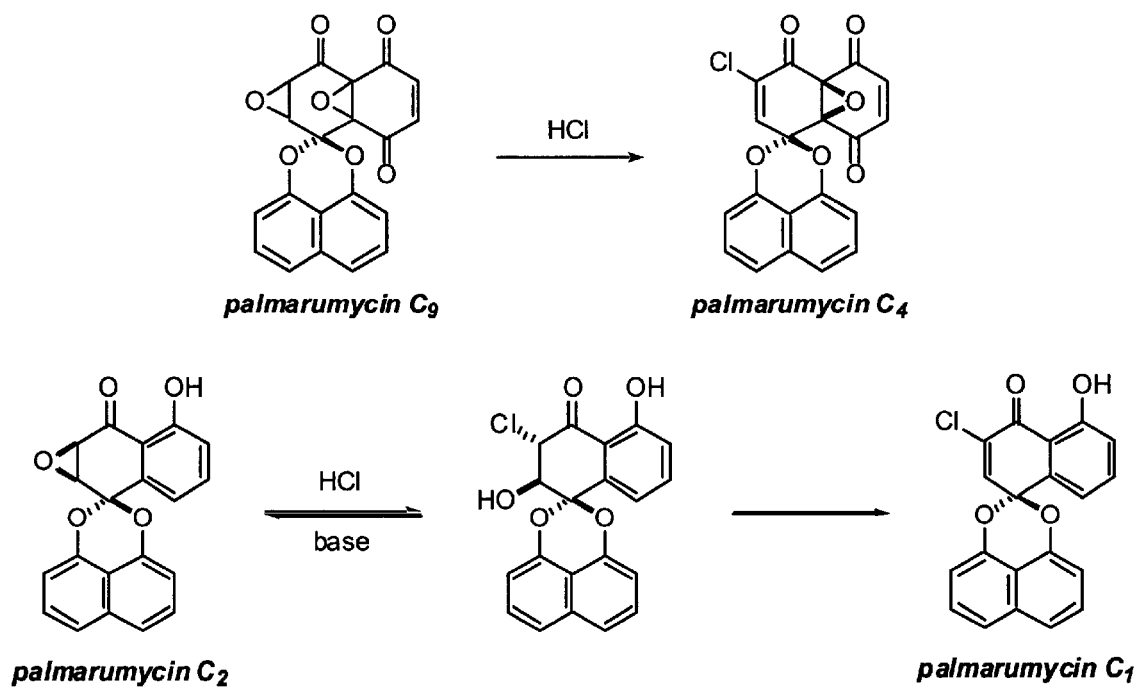
Figure 7
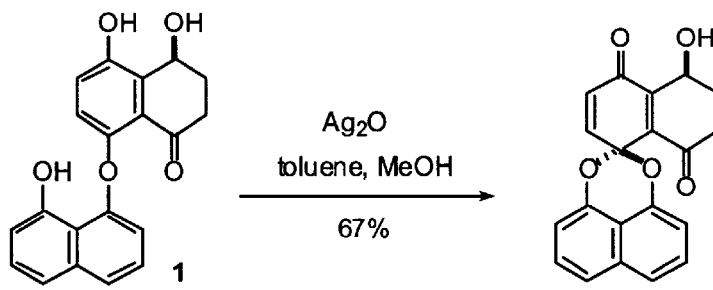
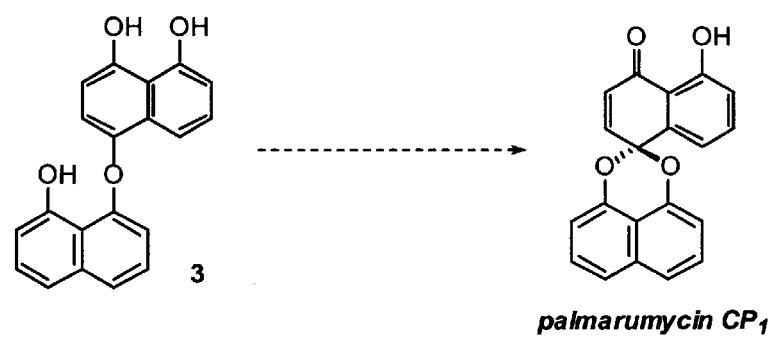
Figure 8

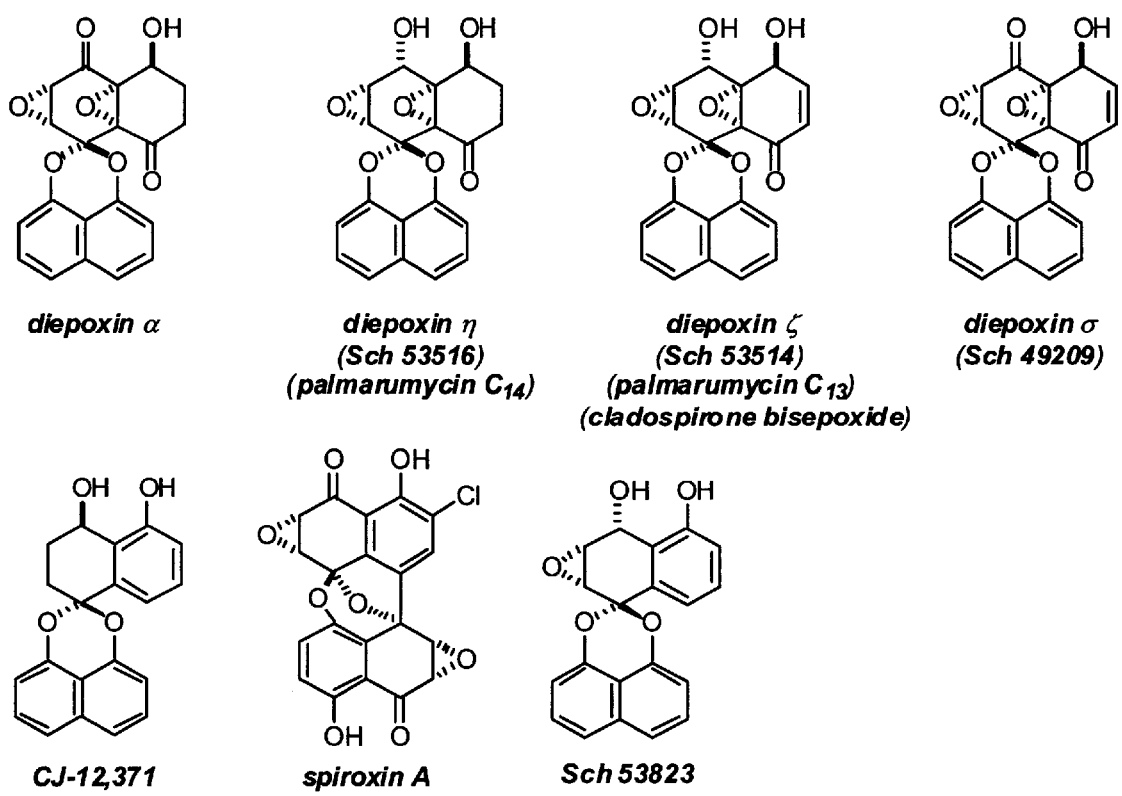
Figure 9 - Representative structurally related fungal metabolites
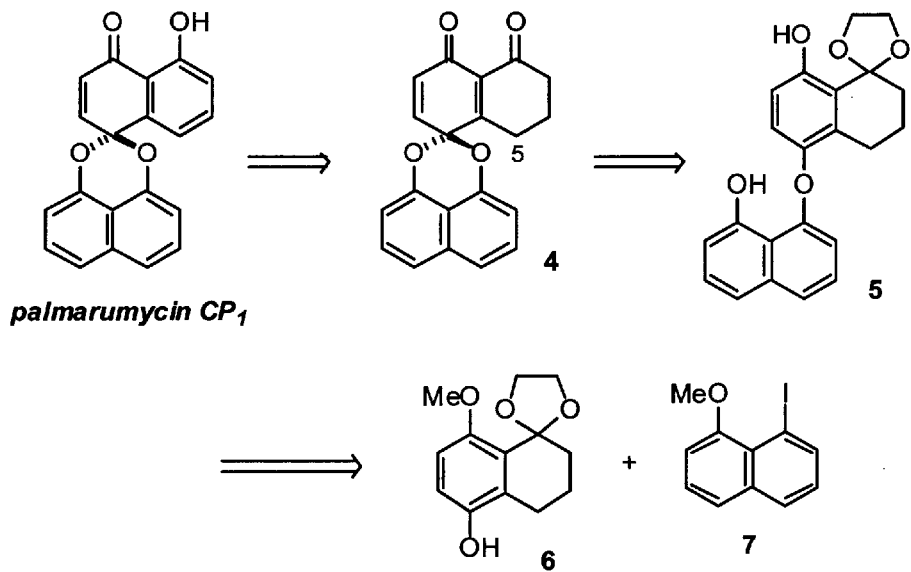
Figure 10

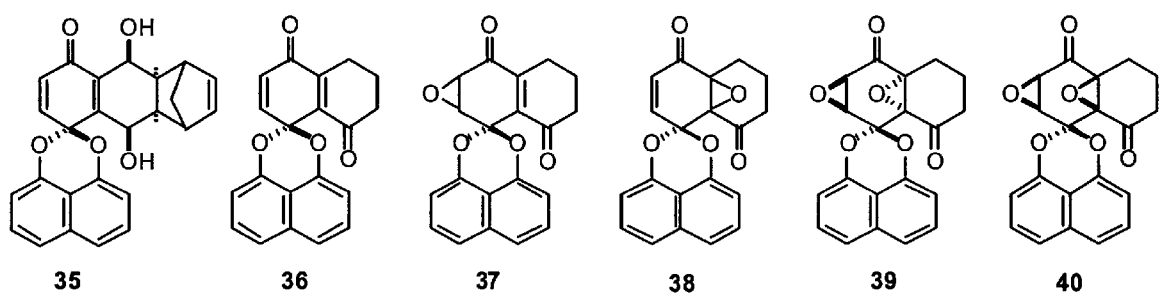
Figure 21 - Deoxypreussomerin A and diepoxin σ analogs
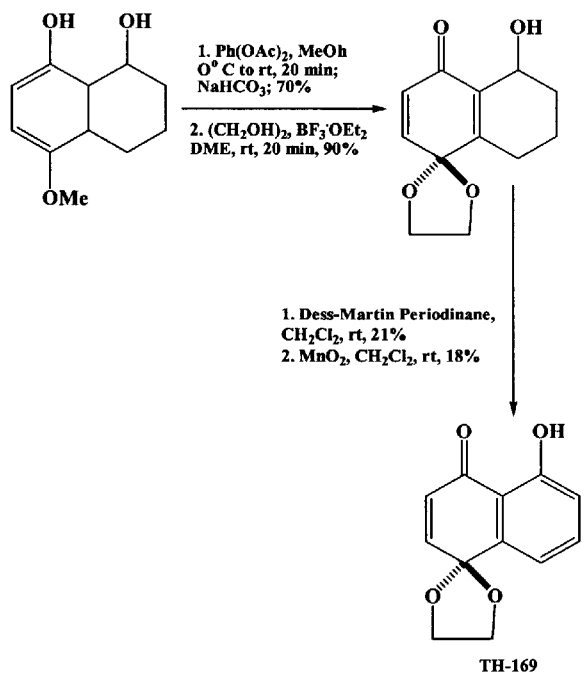
Figure 22A
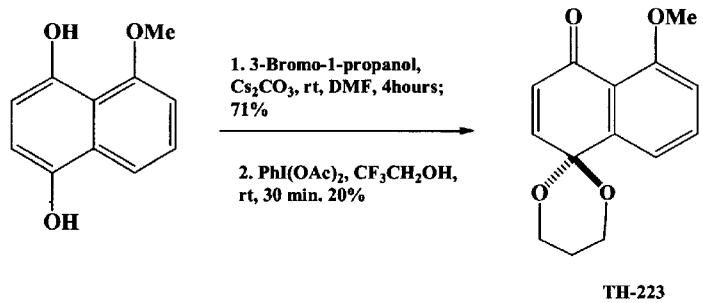
Figure 22B

SYNTHESES AND METHODS OF USE OF NEW ANTIMITOTIC AGENTS

This application claims the benefit of U.S. Provisional Application No. 60/219,282 filed Jul. 19, 2000.

Statement Regarding Federally-Sponsored Research

This invention was supported by the United States Government under Grant No. CA-78039 awarded by the National Institutes of Health. The Government may have certain rights in the invention.

FIELD OF THE INVENTION

The present invention relates in general to anticancer agents, and more specifically to synthetic analogs of deoxypreussomerin, palmarumycin $CP_1$ and related naphthoquinone spiroketals, which exhibit antimitotic activity.

BACKGROUND OF THE INVENTION

The cell cycle consists of series of stages abbreviated G1- S - G2 - M. G1 stands for gap number 1; S for synthesis (DNA synthesis occurs); G2 for gap number 2 and M for mitosis or cell division. Control of cell division is very complex and involves regulation at a number of levels. In cancerous cells, the normal regulatory processes are somehow disrupted and cell growth is uncontrolled.

Tubulin is a protein that polymerizes into long chains or filaments that form microtubules. Microtubules are hollow fibers, which serve as kind of a skeletal system for living cells. Microtubules have the ability to shift through various formations, thus allowing the cell to undergo mitosis. The formation-shifting of microtubules is made possible by the flexibility of tubulin monomers, especially in the presence of agents/drugs and proteins that bind tubulin.

Interest in tubulin has increased recently because a natural substance (paclitaxel) found in the bark of the Pacific yew tree, was shown in clinical tests to be an effective treatment for a number of cancers including ovarian, breast, and lung. Paclitaxel prevents cell division by promoting the assembly of and inhibiting the disassembly of microtubules.

Cell cycle checkpoints are critical regulators of genome integrity and faithful cell replication. One of the main abnormalities in human tumors cells is the loss of the G1 phase checkpoint, which not only permits cellular replication but also encourages genomic instability. Consequently, enforcement of the G2/M checkpoint represents an attractive mode of action for new antineoplastic agents. G2/M progression is tightly regulated by several cellular macromolecules, including tubulins, and microtubule-associated proteins and motor proteins, such as kinesins and dynesins. An additional essential regulator is the maturation/ M-phase promoting factor comprising Cdk1/cyclin B. Cdk1/ cyclin B itself is regulated by a complex group of positive and negative regulating kinases. In mammalian cells, these include weel, mytt, cyclin activating kinase, Chk1 and cds1 kinases. In addition, Cdc25 phosphatases, which are also regulated by other kinases and phosphatases, are responsible for the activation of Cdk1.

Inhibitors of tubulin polymerization or depolymerization are widely available but only a few disrupters of other regulators of G2/M progression have been identified. For example, several small molecule inhibitors of Cdc25 that block G2/M progression have been identified, but those compounds also affect G1 transition (Tamura K, Rice RL, Wipf P and Lazo JS (1999) Dual G1 and G2/M phase inhibition by SC-ααδ9, a combinatorially derived Cdc25 phosphatase inhibitor. Oncogene 18:6989–6996, Tamura K, Southwick EC, Kerns J, Rosi K, Carr BI, Wilcox C and Lazo JS (2000) Cdc25 inhibition and cell cycle arrest by a synthetic thioalkyl vitamin K analogue. Cancer Res 60:1317–1325). Others have recently isolated a novel mitotic blocker that appears to act as a specific inhibitor of a mitotic kinesin (Mayer TU, Kapoor TM, Haggarty SJ, King RW, Schreiber SL and Mitchison TJ (1999) Small molecule inhibitor of mitotic spindle bipolarity identified in a phenotype-based screen. Science 286:971–974). Nonetheless, there continues to be a great need for pharmacologically distinct agents both to investigate the G2/M progression process and as new pharmacophores for drug design strategies.

The antifungal metabolites, preussomerins A–F, were identified in 1990 by Gloer and coworkers during the course of an investigation of chemical agents involved in interspecies competition among coprophilous (dung-colonizing) fungi. (Weber, H. A.; Baenziger, N. C.; Gloer, J. B. *J Am. Chem. Soc.* 1990, 112, 6718). In addition to those early reports from *Preussia isomera* Cain samples, preussomerins were later also discovered in the endophytic fungus *Harmonerna dematioides* (Polish J. D.; Dombrowski, A. W.; Tsou, N. N.; Salituro, G. M.; Curotto, J. E. *Mycologia* 1993, 85, 62). Other reports of an epoxy naphthalenediol spiroketal compound, bipendensin, have been published (Connolly, J. D. *4th International Symposium and Pakistan-US. Binational Workshop on Natural Products Chemistry*, Karachi, Pakistan, January 1990 and Connolly, J. D.: *Structural elucidation of some natural products. In Studies in Natural Products Chemistry*, Vol 9. Ed., Atta-ur-Rahman, pp. 256–258, Elsevier Science Publishers B. V., Amsterdam, 1991). Bipendensin was isolated in very small amounts from wood samples of the African tree *Afzelia bipendensis*. A compound having the same gross structure as bipendensin was isolated in 1994 from an unidentified Coniothyium fungus collected from forest soil on West Borneo, and was named palmarumycin $C_{11}$, (Krohn, K.; Michel, A.; Florke, U.; Aust, H.-J.; Draeger, S.; Schulz, B. *Liebigs Ann. Chem.* 1994, 1099).

The pentacyclic palmarumycins are structurally unique natural products with both antifungal and antibacterial activities, but their antineoplastic effects are not well established. The naphthoquinone acetals, palmarumycins, diepoxins and deoxypreussomerins are structurally unique fungal metabolites with both antifungal and antibacterial activities, but their antiproliferative activity against malignant mammalian cells has not been extensively studied. (Wipf, P and June JK (1998) Total synthesis of palmarumycin CP1 and (±)-deoxypreussomerin A. J Org Chem 63:3530–3531: Schlingmann GRR, West LP, Milne CJ and Carter GT (1993) Diepoxins, novel fungal metabolites with antibiotic activity. Tetrahedron Lett 34:7225–7228: Krohn K, Michel A, Florke U, Aust H-J, Draeger S and Schulz B (1994) Palmarumycins C1–C6 from Coniothyrium: Isolation, structure elucidation, and biological activity. Liebigs Ann Chem 1994:1099–1108). Biological studies have been limited due to the extraordinary synthetic challenges associated with the extensive levels of oxygenation and the highly electrophilic functionality present in these spiroketal natural products.

Since its discovery in the early 1960s, the thioredoxin— thioredoxin reductase system has been the subject of intense pharmacological studies (Williams,C.H. *Eur.JBiochem.* 2000, 267, 6101). The two redox active proteins have been isolated from many species, and their medical interest is based in part on their value as indicators of widespread diseases such as rheumatoid arthritis, AIDS, and cancer. The cytosolic 12 kDa thioredoxin-1 (Trx-1) is the major cellular protein disulfide reductase and its dithiol-disulfide active site cysteine pair (CXXC) serves as electron donor for enzymes such as ribonucleotide reductase, methionine sulfoxide reductase, and transcription factors including NF-κB and the Ref-1-dependent AP-1 (Arn r,E.S.J.; Holmgren,A. *Eur.JBiochem.* 2000, 267, 6102). Therefore, thioredoxin-l is critical for cellular redox regulation, signaling, and regulation of protein function as well as defense against oxidative stress and control of growth and apoptosis. (Davis,W.; Ronai,Z.; Tew,K.D. *JPharm.Exp. Ther.* 2001, 296, 1). Thioredoxin-1 acts in concert with the glutathione—glutathione reductase system but with a rate of reaction orders of magnitude faster,and lack of cytosolic mammalian thioredoxin is embryonically lethal. Eukaryotic thioredoxin reductases (TrxR) are 112–130 kDa, selenium-dependent dimeric flavoproteins that also reduce substrates such as hydroperoxides or vitamin C (Williams, C.H.; Arscott, L.D.; Miller,S.; Lennon,B.W.; Ludwig,M.L.; Wang,P.-F.; Veine,D.M.; Becker,K.; Schirmer,R.H. *Eur.JBiochem.* 2000, 267,6110). These reductases contain redox-active selenylsulfide-selenolthiol active sites and are inhibited by aurothioglucose and auranofin (K; 4 nM). (Becker,K.; Gromer,S.; Schirmer, R.H.; Mller,S. *Eur.JBiochem.*2000, 267, 6118). NADPH serves as reducing agent of Trx-1 via TrxR.

Pathophysiological effects of Trx-1/TrxR are indicated by Trx-1 overexpression in human tumors such as lung, colorectal and cervical cancers and leukemia, and secreted Trx-1 stimulates cancer cell growth and decreases sensitivity to induced apoptosis (Powis,G.; Kirkpatrick,D.L.; Angulo, M.; Baker,A. *Chem.-Biol.Interactions* 1998, 111 ,23). The Trx-1/TrxR system is therefore an important target for chemotherapeutic intervention. Alkyl 2-imidazolyl disulfides were found to be inhibitors of Trx-1/TrxR with $IC_{50}$'s of 31/37 μM, respectively; these disulfides block MCF-7 human breast cancer cells in the G2/M phase of the cell cycle and suppress the growth of several human primary tumors in the NCI 60 cancer cell line panel (Vogt,A.; Tamura,K.; Watson,S.; Lazo,J. S. *J. Pharm.Exp.Ther.* 2000, 294 ,1070). A COMPARE analysis revealed the most potent Trx-1/TrxR inhibitor known to date, the para-quinone NSC401005 which is the natural product pleurotin (Kunkel, M.W.; Kirkpatrick,D.L.; Johnson,J.I.; Powis,G.*Anti-Cancer Drug Des.* 1997, 12, 659). The IC 50 of NSC401005 was determined as 0.17 μM; however, the average GI 50 of this compound in the 60 cell line panel was only 21.5 μM. Although inhibitors of TrxR such as auranofin and nitrosoureas are quite effective, the search for new, more specific, and less toxic compounds is well justified.

Therefore, a need exists in the art for new chemical compounds that block G2/M phase transition. Such compounds would find use as pharmacological probes and possible lead structures for therapeutic agents. These compounds may include inhibitors of the thioredoxin—thioredoxin reductase system which are less toxic than current compounds.

SUMMARY OF THE INVENTION

The inventors have developed an efficient synthetic approach toward palmarumycins, diepoxins and deoxypreussomerins and have generated a library of analogs. A number of these analogs inhibit the thioredoxin—thioredoxin reductase system. The inventors have examined the antiproliferative actions of pentacyclic palmarumycins against tumor cells using a temperature sensitive tsFT210 mouse mammary carcinoma cell line and found that a new palmarumycin analog, [8-(furan-3-ylmethoxy)-1-oxo- 1,4-dihydronaphthalene-4-spiro-2 '-naphtho[ 1",8"-de] [1',3'] [dioxin] herein termed SR-7, prominently blocked mammalian cell cycle transition in G2/M but not in G1 phase. The inventors found no evidence for inhibition of the critical mitosis-controlling cyclin-dependent kinase, Cdk1, or its regulator, the dual specificity phosphatase Cdc25. Moreover, Cdk1 was hypophosphorylated and not directly inhibited by SR-7. SR-7 also failed *in vitro* to hypernucleate bovine tubulin, did not compete with colchicine for tubulin binding, and only modestly blocked GTP-induced assembly. In addition, SR-7 caused almost equal inhibition of paclitaxel-sensitive and -resistant cell growth. Moreover, unlike benchmark tubulin disrupting agents, SR-7 did not cause hyperphosphorylation of the antiapoptotic protein Bcl-2. Thus, SR-7 can inhibit G2/M transition by a mechanism that appears to be independent of marked tubulin disruption.

These and other advantages and benefits of the present invention will be apparent from the Detailed Description of the Invention herein below.

BRIEF DESCRIPTION OF THE FIGS.

The present invention will now be described for the purpose of illustration and not limitation in conjunction with the following figures wherein:

FIG. 1 shows the absolute stereochemistry of the preussomerins;

FIG. 2 depicts the acidic degradation of preussomerin A;

FIG. 3 illustrates preussomerins and deoxypreussomerins isolated from a coelomycetes fungus;

FIG. 4 shows reaction of preussomerin G with strong nucleophile;

FIG. 5 depicts palmarumycins from Coniothyriumpalmarium;

FIG. 6 illustrates palmarumycins from an unidentified Coniothyriu species;

FIG. 7 illustrates treatment of palmarumycin $C_9$ and palmarumycin $C_2$ with methanolic HCl;

FIG. 8 shows cyclization of binaphthyl ether;

FIG. 9 depicts representative structurally related fungal metabolites;

FIG. 10 shows a potential synthetic strategy toward palmarumycin CP1 and deoxypreussomerin A;

Figure 19A:
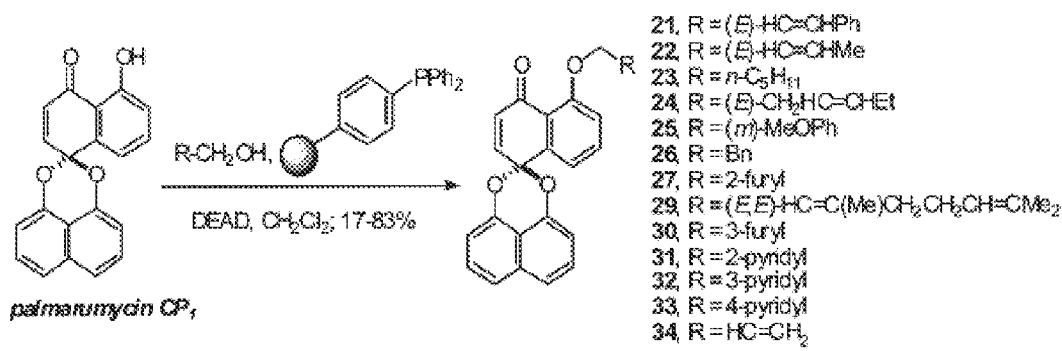
Figure 20:
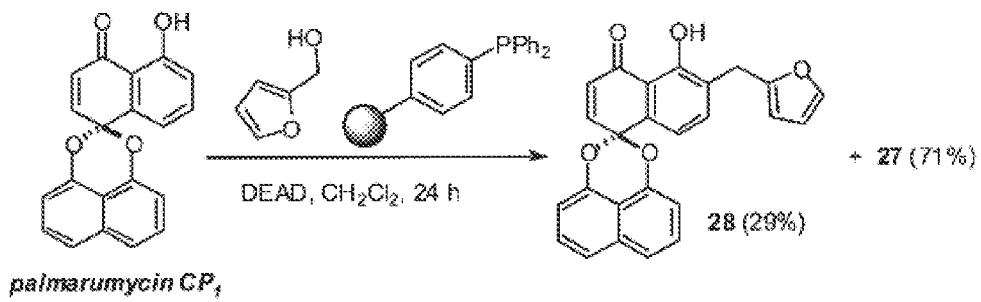
Figure 23:
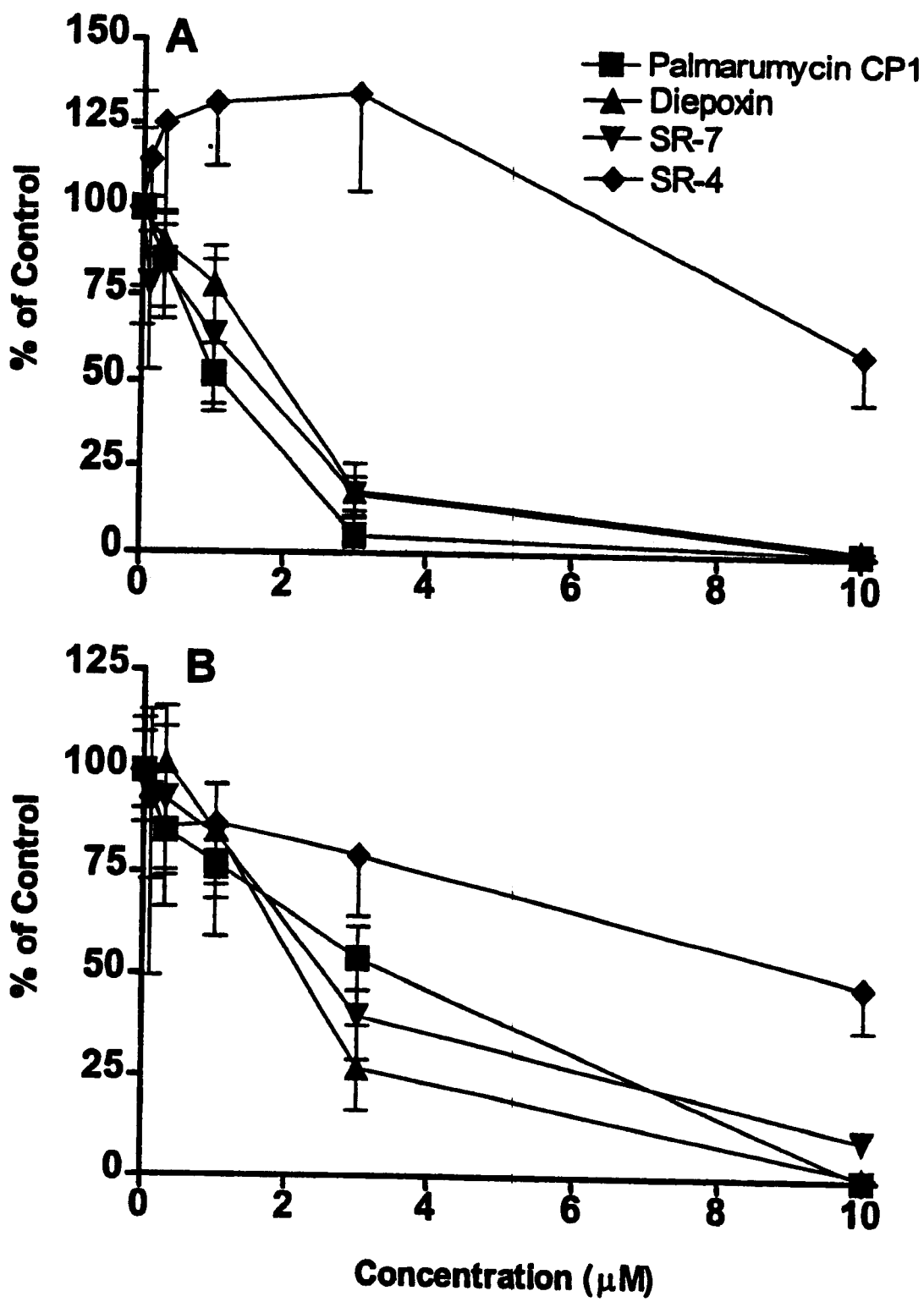
Figure 24:
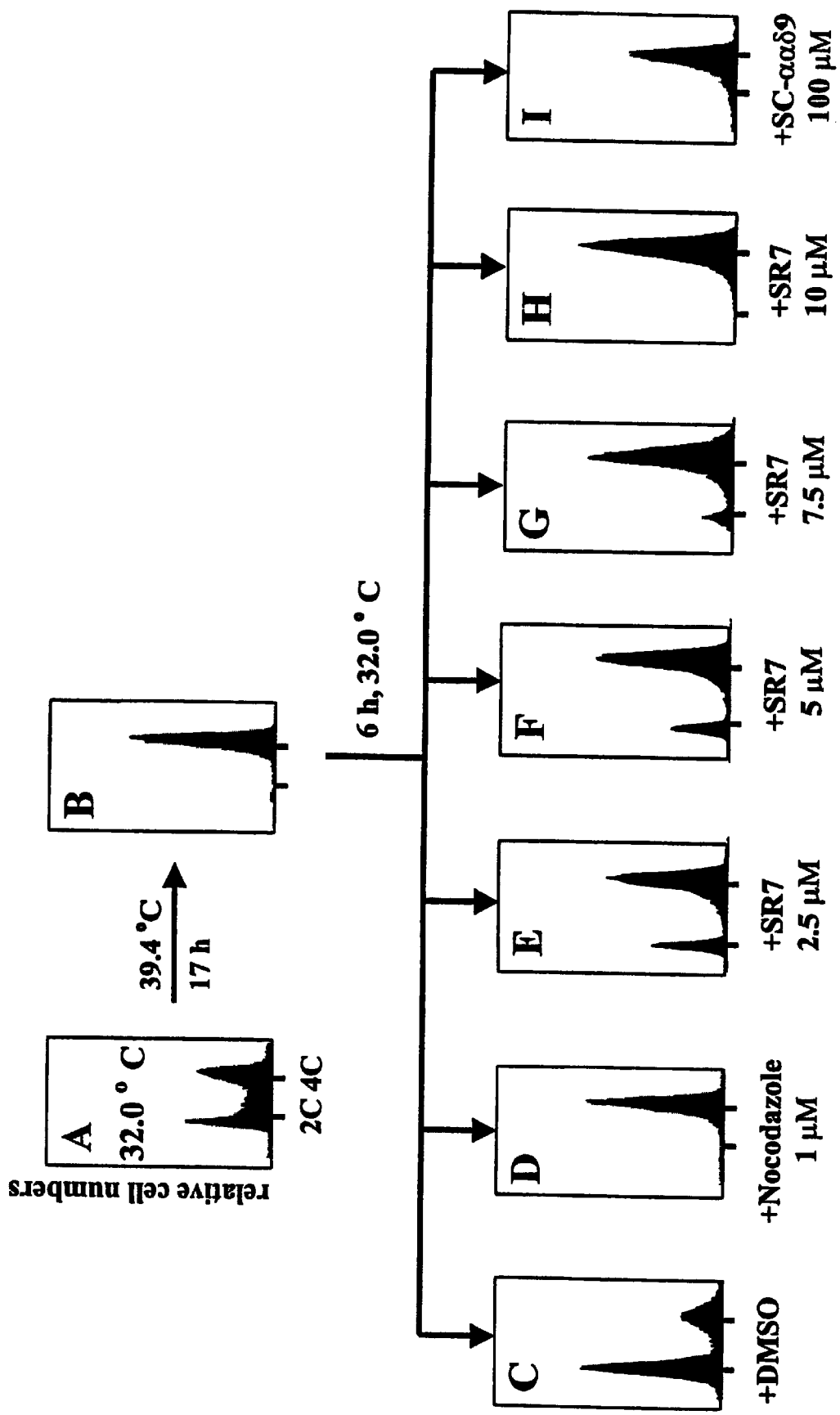
Figure 25:
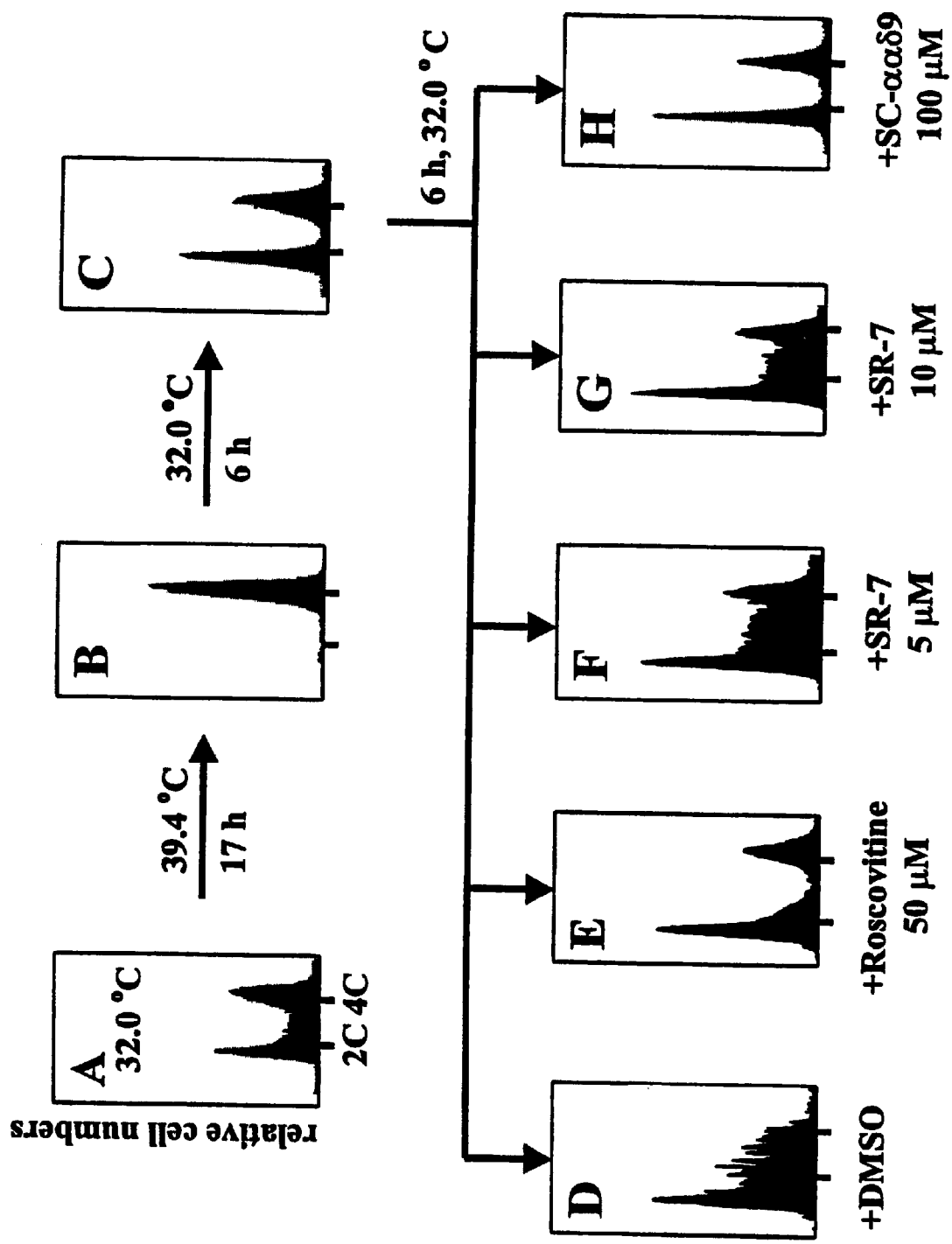
Figure 26:
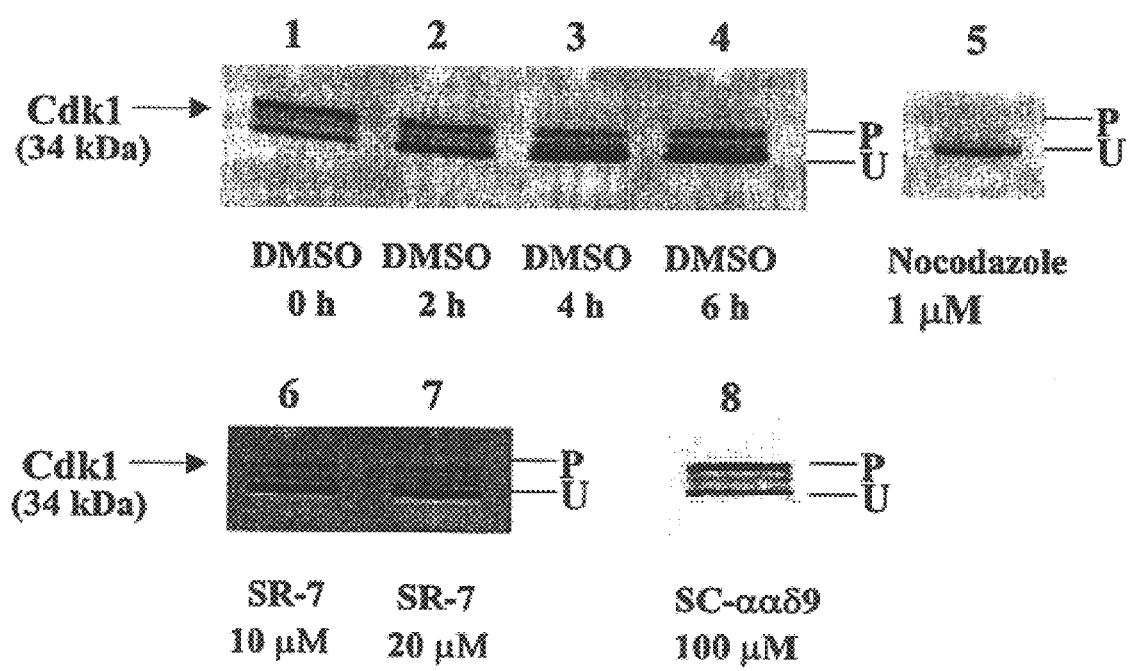
Figure 27:
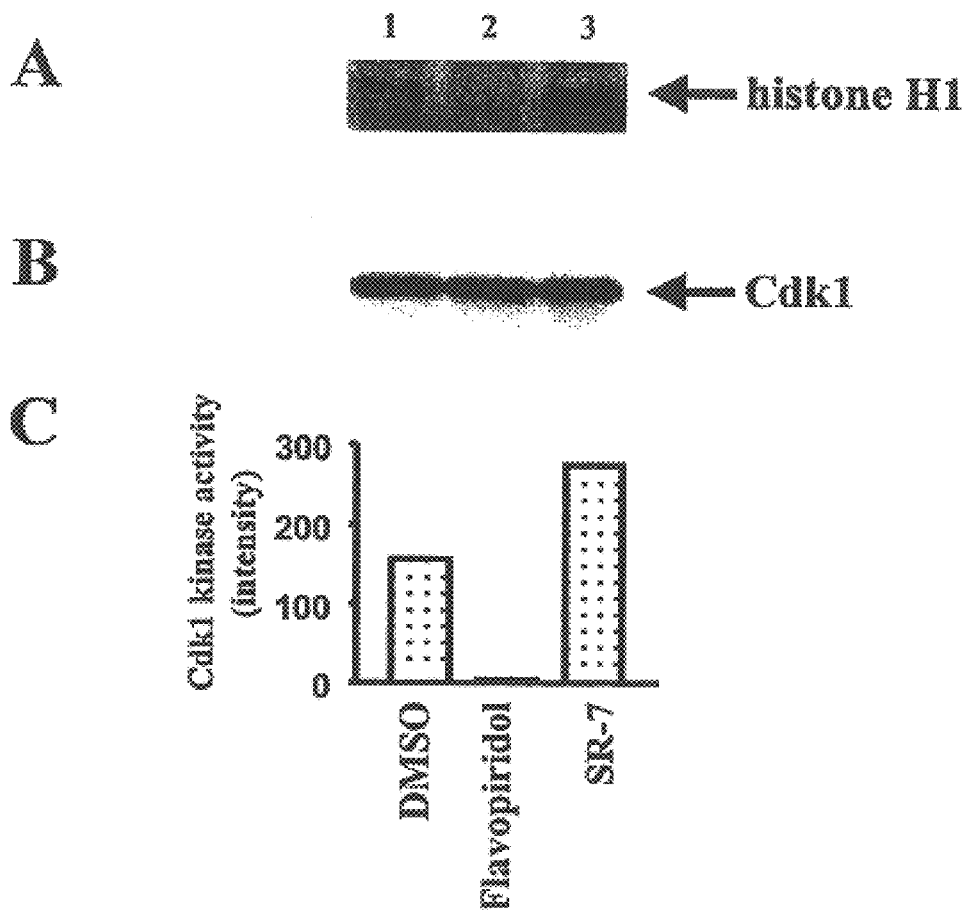
Figure 28:
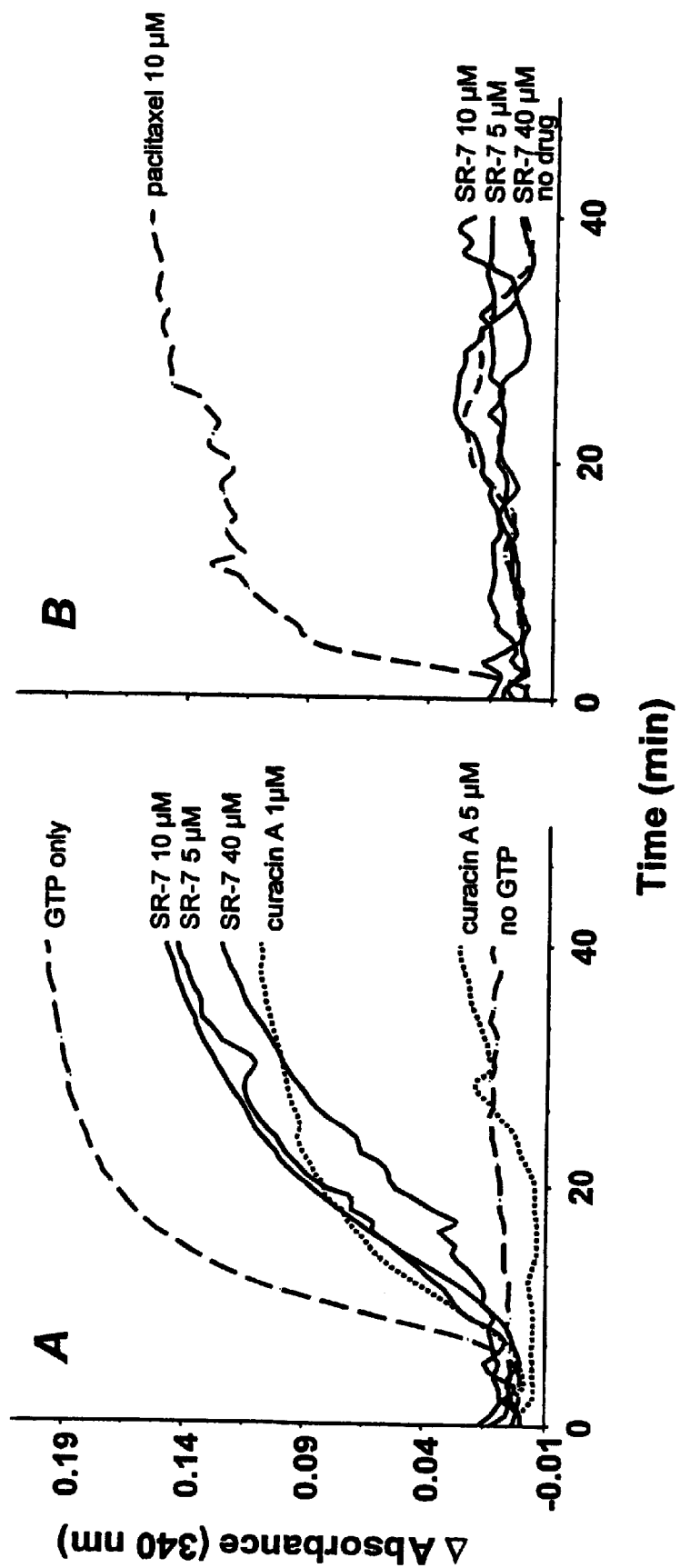

FIGS. 19A and B show generation of analogs from palmarnmycin $CP_1$;

FIG. 20 depicts treatment of palmarumycin $CP_1$ with 2-f\uryl methanol;

FIG. 21 illustrates deoxypreussomerin A and diepoxin analogs;

FIGS. 22A and B show the syntheses of TH-169 and TH-223;

FIG. 23 illustrates cytotoxicity and G2/M phase inhibition by SR-7;

FIG. 24 illustrates cell growth inhibition of murine tsFT210 cells;

FIG. 25 shows G1 transition in tsFT210 cells after treatment with SR-7;

FIG. 26 illustrates Cdk1 dephosphorylation in the presence of SR-7;

FIG. 27 depicts the ability of SR-7 to directly inhibit Cdk1 kinase activity;

FIG. 28 shows SR-7 effect on tubulin assembly; and

Figure 29:
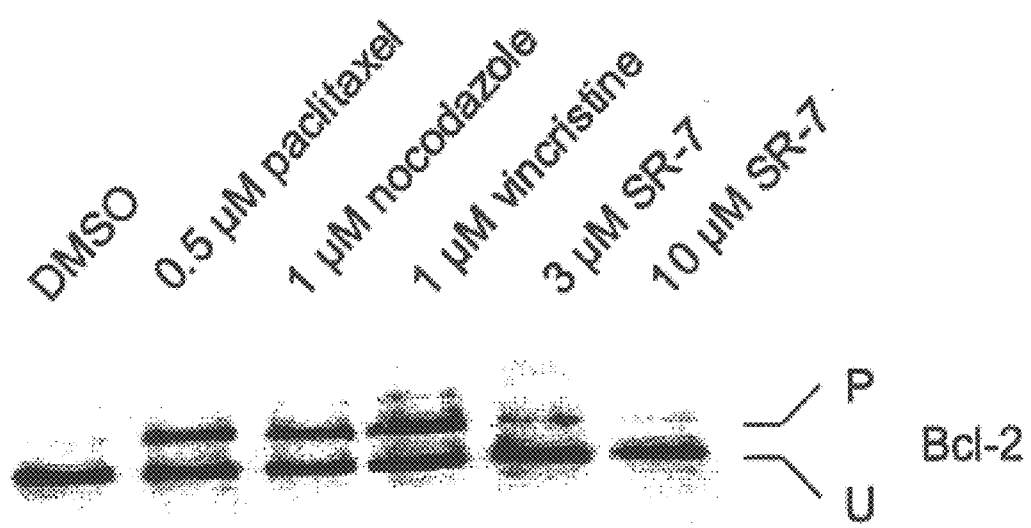

FIG. 29 depicts effects of SR-7 on Bcl-2 phosphorylation.

DETAILED DESCRIPTION OF THE INVENTION

The following abbreviations are used herein: Cdk is cyclin dependent kinase; DMSO is dimethyl sulfoxide; SC-ααδuoa9 is 4-(benzyl-(2-[ (2,5-diphenyl-oxazole-4-carbonyl)-amino]-ethyl)-carbamoyl)-2-decanoylamino butyric acid; and SDS-PAGE is sodium dodecyl sulfate-polyacrylamide gel electrophoresis. The references cited in this detailed description of the present invention, to the extent that they provide exemplary procedural or other details supplementary to those set forth herein, are specifically incorporated herein by reference.

The synthesis and initial antiproliferative evaluation of the palmarumycin/diepoxin analogs have been described elsewhere (Wipf P, Jung J-K, Rodriguez S, Lazo JS Synthesis and biological evaluation of Deoxypreussomerin A and Palmarumycin CP 1 and related naphthoquinone spiroketals. Tetrahedron 57:283–296 (2001)). The synthesis, biochemical and cellular properties of the Cdc25 inhibitor, SC-ααδ9, have also previously been published (Rice RL, Rusnak JM, Yokokawa F, Yokokawa S, Messner DJ, Boynton AL, Wipf P and Lazo JS (1997) A targeted library of small molecule, tyrosine and dual specificity phosphatase inhibitors derived from a rational core design and random side chain variation. Biochemistry 36:15965–15974), (Tamura K, Rice RL, Wipf P and Lazo JS (1999) Dual G1 and G2/M phase inhibition by SC-ααδ9, a combinatorially derived Cdc25 phosphatase inhibitor. Oncogene 18:6989–6996.). Curacin A was prepared as described previously (Wipf P and Xu W (1996) Total synthesis of antimitotic marine natural product (+)-curacin A. J Org Chem 61:6556–6559.).

tsFT210 cells, which contain a temperature sensitive mutant form of Cdk1 allowing for convenient cell cycle synchronization, were a gift from Dr. Chris Norbury (Oxford University, Oxford, UK) and were maintained for no longer than 30 passages (Th'ng JP, Wright PS, Hamaguchi J, Lee MG, Norbury CJ, Nurse P and Bradbury EM (1990) The FT210 cell line is a mouse G2 phase mutant with a temperature-sensitive CDC2 gene product. Cell 63:313–324.). Paclitaxel-resistant (1 A9/PTX10, 1 A9/PTX22) and parental 1 A9 human ovarian carcinoma cells were gifts from Drs. Paraskevi Giannakakou and Tito Fojo of the National Cancer Institute (Bethesda, Md.). The SV-40 large T antigen transformed cells have been previously characterized (Vogt A, Wang AS, Johnson CS, Fabisiak JP, Wipf P and Lazo JS (2000) In vivo antitumor activity and induction of insulin-like growth factor-1 resistant apoptosis by SC-ααδ9. J Pharmacol Exptl Therap 292:530–537.). AntiCdk1 (sc-54), antiCdc25, and antiBcl-2 (sc-509) antibodies were purchased from Santa Cruz Biotechnology (Santa Cruz, Calif.). An agarose conjugate of antiCdk1 was used for immunoprecipitation. Histone H1 was obtained from Boehringer Mannheim Co. (Indianapolis, Ind.) and [γ-$^{32}$P]ATP (1 OmCi/mmol) was from Amersham Life Science, Inc. (Arlington Heights, Ill.). [ring C, methoxy-$^3$H] colchicine (61.4 Ci/mmol, 2.3TBq/mmol) was from NEN (Boston, Mass.). Paclitaxel was obtained from the Drug Synthesis Branch of the National Cancer Institute. All other reagents were from Sigma Co. (St. Louis, Mo.) unless indicated otherwise.

The absolute stereochemistry of preussomerins has been assigned as shown in FIG. 1 on the basis of the isolation of known (−)-regiolone as a degradation product (Preussomerins A–F: Weber, H. A.; Gloer, J. B. *J. Org. Chem.* 1991, 56, 4355). Although the ketal linkages are resistant to acid hydrolysis at room temperature, vigorous cleavage conditions (6 M HCl/ acetone, 1:1, 100 ° C., 12 h) yield (−)-regiolone as the major product (Talapatra, S. L.; Karmacharya, B.; Shambhu, C. D.; Talapatra, B. *Phytochemistry* 1988, 27, 3929). Without being limited to any specific theory, the inventors believe that conservation of the stereochemistry at the C- 1 ' position could be rationalized by a mechanism involving protonation at the C-2' position during the decomposition process followed by loss of the 9-OH proton and formation of an enol ether. This reaction is shown in FIG. 2. Hydrolysis of the remaining ketal linkage would account for the formation of regiolone without loss of stereochemical integrity at the hydroxylated benzylic carbon.

Even though preussomerin A has been reported to exhibit only low-micromolar cytotoxicity toward a mammalian cell line, (Preussomerins A–F: Weber, H. A.; Gloer, J. B. *J. Org. Chem.* 1991, 56, 4355) a research group reported that preussomerins and deoxypreussomerins showed promising effects as ras famesyl-protein transferase (FTPase) inhibitors (Singh, S. B.; Zink, D. L.; Liesch, J. M.; Ball, R. G.; Goetz, M. A.; Bolessa, E. A.; Giacobbe, R. A.; Silverman, K. C.; Bills, G. F.; Pelaez, F.; Cascales, C.; Gibbs, J. B.; Lingham, R. B. *J. Org. Chem.* 1994, 59, 6296).

Preussomerin G–I and deoxypreussomerin A and B, accompanied by preussomerin D, were isolated from the fermentation broth of an unidentified coelomycetes fungus collected in Bajo Verde, Argentina. Structures of those compounds are shown in FIG. 3. $IC_{50}$'s of FTPase inhibitory activities of preussomerins, deoxypreussomerins and derivatives of preussomerin G range between 1–20 μM. Preussomerin G and preussomerin D were the most active. Interestingly, deoxypreussomerins, which possibly are biosynthetic precursors of preussomerins had equal or better activities than preussomerins H and I. Deoxypreussomerin A and B were also reported independently as antifungal agents and named palmarumycin $C_2$ and $CP_2$, respectively (Krohn, K.; Beckmann, K.; Florke, U.; Aust, H.-J.; Draeger, S.; Schulz, B.; Busemann, S.; Bringmann, G. *Tetrahedron* 1997, 53, 3101).

Preussomerin G can react with strong nucleophiles in a highly stereospecific Michael fashion to give a quantitative yield of the C-3'adduct as illustrated in FIG. 4. Without being limited to any specific theory, the inventors believe that steric hindrance may make the top face of preussomerin G inaccessible to nucleophiles, and thus Michael addition can take place exclusively from the more accessible α-face.

Additional naphthalenediol spiroketals of the palmarumycin family have been reported in the literature (Krohn, K.; Beckmann, K.; Flörke, U.; Aust, H.-J.; Draeger, S.; Schulz, B.; Busemann, S.; Bringmann, G. *Tetrahedron* 1997, 53, 3101). Those metabolites produced by *Coniothyrium palmarium*, are shown in FIG. 5 and those produced by an unidentified Coniothyrium species are shown in FIG. 6.

Palmarumycin $CP_3$, $CP_4$, $C_3$, $C_{10}$ and $C_{12}$ show high antifungal activity. It is theorized that the introduction of an oxygen function into the 8-position significantly increases the antifungal effect. The chloroepoxide palmarumycin $C_4$ and palmarumycin $C_9$, isolated as an isomeric mixture of epoxides, completely inhibited germination and growth of garden cress. In most palmarumycins, only the relative configuration was elucidated, except for palmarumycin $CP_{4a}$ and $CP_5$. The absolute configurations of the latter compounds were elucidated by calculations. After computation of the circular dichroism (CD) spectra of six low energy conformers, Boltzmann-weighted addition and comparison of the resulting averaged spectrum with the experimental data allowed the assignment of the absolute configuration of palmarumycin $CP_{4a}$ and $CP_5$ as shown in FIG. 5.

Krohn and coworkers proposed a biosynthesis of palmarumycin $CP_1$ based on a 1,8-dihydroxynaphthalene or a suitable phenolic derivative precursor. (See also: Bode, H. B.; Wegner, B.; Zeeck, A. *J. Antibiot.* 2000, 53, 153). According to their hypothesis, coupling could occur via a phenol oxidation as often encountered in polyketide biosynthesis, and the chlorinated palmarumycins could be derived from addition of chloride ions to epoxides. (Herbert, R. B. *The Biosynthesis of Secondary Metabolites*, 2nd ed., Chapman and Hall, London, 1989 and O'Hagen, D. *The Polyketide Metabolites*, Ellis Horwood, New York, 1991). To probe this mechanism, palmarumycin $CP_2$ and pahnarumycin $C_9$ were treated with methanolic hydrochloric acid as shown in FIG. 7. As expected, formation of chlorinated palmarumycin $C_4$ from palmarumycin $C_9$ could be detected by TLC. For the reaction of paimarumycin $C_2$, an intermediate chlorohydrin was identified as the major isomer. This chlorohydrin slowly decomposed to palmarumycin $C_1$ upon standing in chloroform solution. Palmarumycin $C_2$ was recovered upon treatment with base. These experiments suggested to the inventors a possible pathway to the chlorinated palmarumycins and highlighted the unexpected stability of the naphthalenediol spiroketal which is not affected even by heating in acetic acid at 100 °C.

The open chain compound 1, shown in FIG. 8, has been isolated from *Coniothyrium palmarum*. (Krohn, K.; Beckmann, K.; Aust, H.-J.; Draeger, S.; Schulz, B.; Busemann, S.; Bringmann, G. *Liebigs Ann./Recueil* 1997, 2531). This isolation offered the chance to probe the biosynthetic hypothesis involving phenol oxidation. Upon exposure to silver(II) oxide, the binaphthyl ether 1 cyclized to yield quinone ketal 2 as depicted in FIG. 8. However, ketal 2 could not be detected in the fermentation broth of *Coniothyrium palmarum*. It is possible that a total synthesis of palmarumycins based on the phenolic oxidation of binaphthyl ethers could be achieved from compound 3, however, the inventors are unaware of further studies along these lines. Others have investigated a biomimetic cyclization approach with little success. (Ragot, J. P.; Alcaraz, M.-L.; Taylor, R. J. K. *Tetrahedron Lett.* 1998, 39, 4921).

Deoxypreussomerins and palmarumycins are structurally closely related to the more recently isolated diepoxins (Schlingmann, G.; West, R. R.; Milne, L.; Pearce, C. J.; Carter, G. T. *Tetrahedron Lett.* 1993, 34, 7225: Schlingrnann, G.; Matile, S.; Berova, N.; Nakanishi, K.; Carter, G. T. *Tetrahedron* 1996, 52, 435), to CJ-12,371 and CS-12,372 (Sakemi, S.; Inagaki, T.; Kaneda, K.; Hirai, H.; Iwata, E.; Sakakibara, T.; Yamauchi, Y.; Norcia, M.; Wondrack, L. M. *J. Antibiot.* 1995, 48, 134) and to spiroxins (McDonald, L. A.; Abbanat, D. R.; Barbieri, L. R.; Beman, V. S.; Discafani, C. M.; Greenstein, M.; Janota, K.; Korshalla, J. D.; Lassota, P.; Tischler, M.; Carter, G. T. *Tetrahedron Lett.* 1999, 40, 2489). Some representative members are depicted in FIG. 9. (For related compounds, see also: (a) Thiergardt, R.; Rihs, G.; Hug, P.; Peter, H. H. *Tetrahedron* 1995, 51, 733, (b) Chu, M.; Patel, M.; Pai, J.-K.; Das, P. R.; Puar, M. S. *Bioorg. Med. Chem. Lett.* 1996, 6, 579,(c) Chu, M.; Truumees, I.; Patel, M.; Das, P. R.; Puar, M. S. *J. Aiztibiot.* 1995, 48, 329, (d) Chu, M.; Truumees, I.; Patel, M. G.; Gullo, V. P.; Pai, J.-K.; Das, P. R.; Puar, M. S. *Bioorg. Med. Chem. Lett.* 1994, 4, 1539, (e) Chu, M.; Truumees, I.; Patel, M. G.; Gullo, V. P.; Puar, M. S.; McPhail, A. T. *J Org. Chem.* 1994, 59, 1222, and (f) Soman, A. G.; Gloer, J. B.; Koster, B.; Malloch, D. *J Nat. Prod.* 1999, 62, 659).

Antimicrobial, antifungal, and some anticancer activities have been identified for diepoxins and spiroxins. The inventors are aware of a research group which isolated the novel fungal metabolites CJ-12,371 and CJ-12,372 from a fermentation broth of an unidentified fungus N983–46. Those compounds showed DNA gyrase inhibitory activity. The phospholipase D inhibitor Sch 53823 has the same gross structure as palmarumycin $C_{11}$, however, the melting point and optical rotation are different, suggesting that palmarumycin $C_{11}$, and Sch 53823 are stereoisomers.

The combination of attractive biological activities and novel structural features in the spirobisnaphthalene family of natural products has attracted considerable interest from the synthetic organic conmmunity. In addition to the pioneering total syntheses of palmarumycin $CP_1$ and deoxypreussomerin (A, Wipf, P.; Jung, J.-K. *J. Org. Chem.* 1998, 63, 3530: Ragot, J. P.; Steeneck, C.; Alcaraz, M.-L.; Taylor, R. J. K. *Perkin Trans.* 1 1999, 1073 and Barrett, A. G. M.; Hamprecht, D.; Meyer, T. *Chem. Commun.* 1998, 809), innovative approaches toward diepoxin α, (Wipf, P.; Jung, J.-K. *Angew. Chem. Int Ed. Engl.* 1997, 36, 764 and Wipf, P.; Jung, J.-K. *J. Org. Chem.* 1999, 64, 1092) preussomerins (G and 1, Chi, S.; Heathcock, C. H. *Org. Lett.* 1999, 1, 3) palmarumycin $CP_2$, palmarumycin $C_1$, and CJ-12,371 have been reported in the art since 1997.

The course of the inventors' work toward the total synthesis of diepoxin (Wipf, P.; Jung, J.-K. Formal Total Synthesis of (+) Diepoxin α *J. Org. Chem.* 2000, 65, 6319) a potential synthetic strategy toward palmarurycin $CP_1$ and deoxopreussomerin A was developed. This strategy is summarized in FIG. 10. Naphthalenediol spiroketal 4 was derived from a binaphthyl ether 5, and dehydrogenation at C(5) and C(6) in 4 should by facilitated be the presence of the enone moiety. Compound 5 can easily be prepared by an Ullmann ether coupling reaction with 1-iodo-8-methoxynaphthalene 7. A modified experimental variant of the method of Graybill et al., was used and the tetraline derivative (Graybill, B. M.; Shirley, D. A. *J. Org. Chem.* 1966, 31, 1221). Example 1

Figure 11:
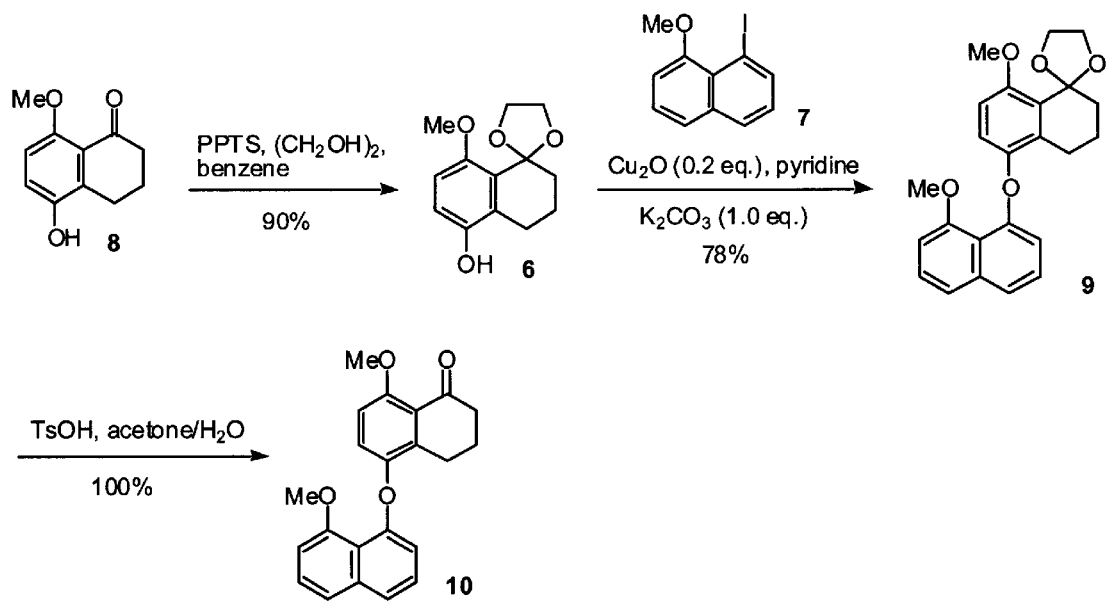
FIG. 11 illustrates preparation of 5-hydroxy-8-methoxy-1 -tetralone.

5-hydroxy-8-methoxy-1-tetralone, compound 8 was prepared by a modified literature procedure (Newhall, W. F.; Harris, S. A.; Holly, F. W.; Johnston, E. L.; Richter, J. W.; Walton, E.; Wilson, A. N.; Folkers, K. *J. Am. Chem. Soc.* 1955, 77, 5646). Attempts for an Ullmann ether coupling between 8 and 8-iodo-1-methoxynaphthalene 7 failed. Without being limited to any specific theory the inventors believe that this failure is quite likely due to the deactivating effect of the tetralone carbonyl group. Coupling with ketal 6 is shown in FIG. 11 was more successful and resulted in a 78% yield of naphthyl ether 9 which was further converted to ketone 10.

Figure 12:
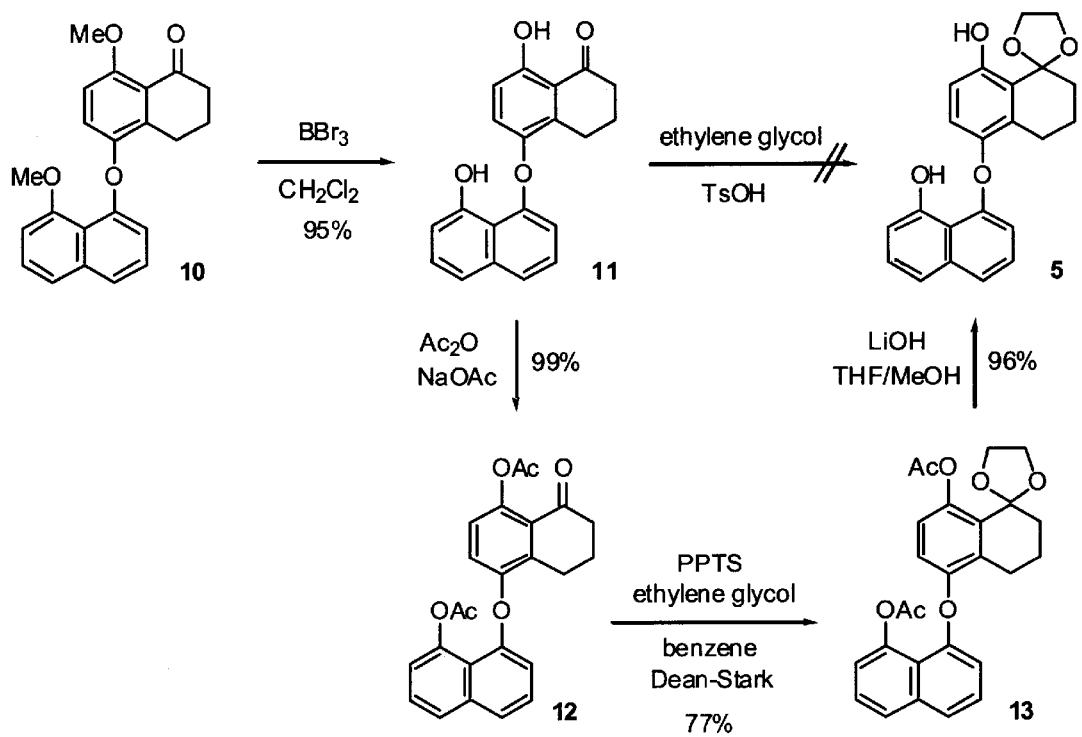
FIG. 12 illustrates preparation of 8-hydroxy-5-(8'-hydroxynaphthalene-1 '-yloxy)-1,2,3,4-tetrahydronaphthalene-1 -spiro-2"-dioxolane.

Although the inventors failed to demethylate ketal 9 with NaSEt in DMF or with $BBr_3$, demethylation of ketone 10 shown in FIG. 12, using $BBr_3$ smoothly yielded compound 11 in 95% yield. The presence of a ketone function in 11 likely will retard the subsequent oxidative cyclization which involves a very electron deficient transition state. Because the ketone function in 11 was unreactive to acetalization conditions, the phenolic hydroxyl groups were first acetylated, and ketal 13 was subsequently saponified to afford the oxidative cyclization precursor 5 in good overall yield as shown in FIG. 12.

Figure 13:
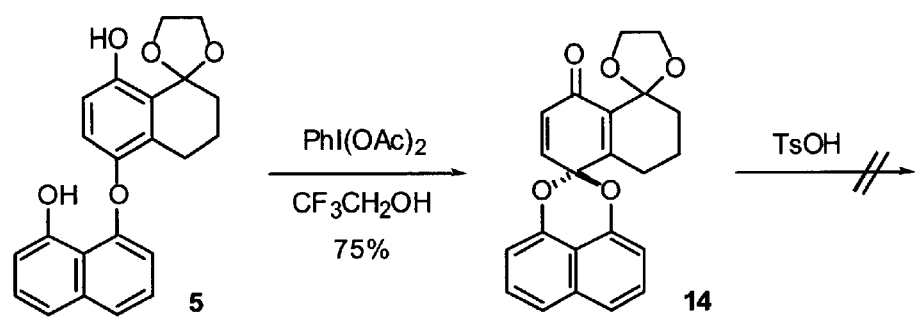
FIG. 13 shows oxidative cyclization of ketal 5.

Oxidative cyclization of ketal 5 with $PhI(OAc)_2$ in trifluoroethanol afforded bisketal 14 in 75% yield is illustrated in FIG. 13. Unfortunately, deprotection of 14 under acidic conditions led to complex mixtures.

Figure 14:
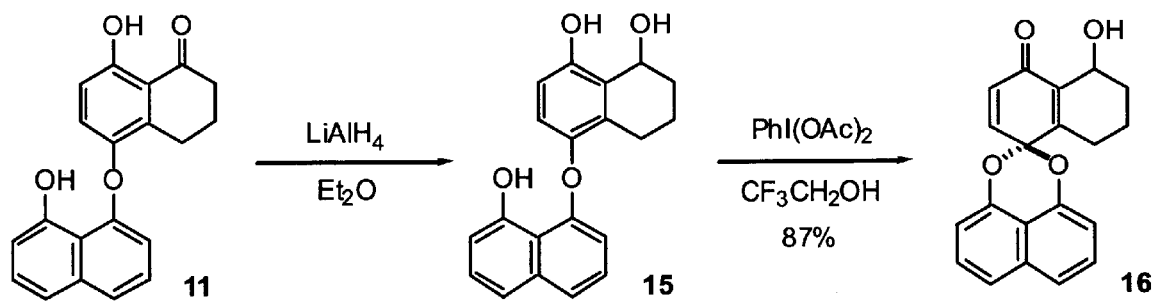
FIG. 14 shows preparation of (±)-8-hydroxy-l-oxo-1,4,5, 6,7,8-hexahydronaphthalene-4-spiro-2'-naphtho [1 ",8"-de] [1',3 ']dioxin.
Figure 15:
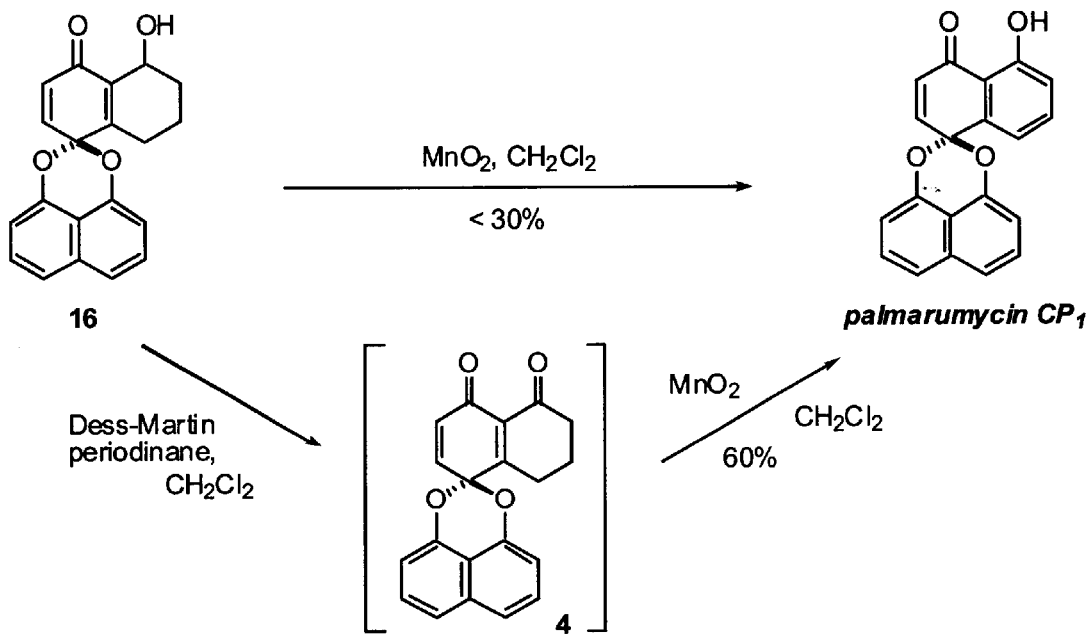
FIG. 15 illustrates conversion of (±)-8-hydroxy-1-oxo-1, 4,5,6,7,8-hexahydronaphthalene-4-spiro-2'-naphtho [1",8"-de] [1',3']dioxin to palmarumycin $CP_1$.

Diol 11 was quantitatively reduced to triol 15, which was oxidatively cyclized using $PhI(OAc)_2$ in trifluoroethanol to afford naphthalenediol spiroketal 16 in 87% yield as depicted in FIG. 14. Further oxidation of the alcohol function of 16 was attempted with PCC and $BaMnO_4$ under buffered conditions, but failed to provide the desired ketone in acceptable yields. In contrast, when 16 was treated with activated $MnO_2$ at room temperature, a clean conversion to the natural product palmarumycin $CP_1$ was effected as shown in FIG. 15. For complete conversion of 16 to palmarumycin $CP_1$, a large excess (more than 50 equivalents) of $MnO_2$ was required, and a considerable amount of product remained adsorbed on $MnO_2$ and could not be recovered. When the reaction was performed in dry benzene at reflux, the amount of $MnO_2$ required for the complete conversion of 16 was decreased to ~10 equivalents, but the resulting palmarumycin $CP_1$ was contaminated with a inseparable byproduct. The inventors therefore used a two-step protocol in which oxidation of 16 with Dess-Martin periodinane, purification of the intermediate ketone by column chromatography on $SiO_2$, and treatment with 10 equivalents of $MnO_2$ in dry methylene chloride for 2 days at room temperature afford the target molecule in 60% yield. Palmarumycin $CP_1$ was thus obtained in 35% overall yield in 8 steps from the known tetralone 8.

Figure 16:
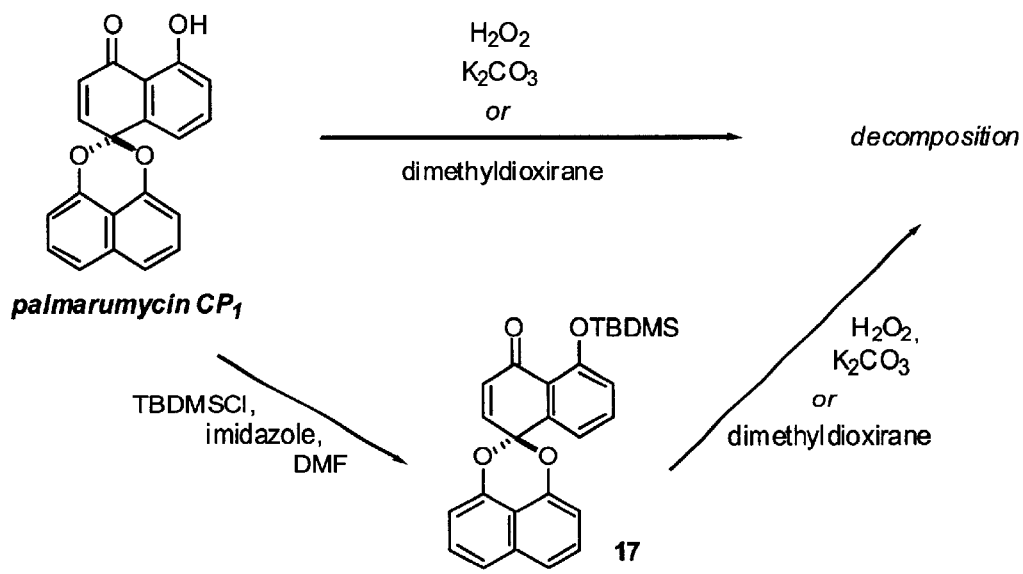
FIG. 16 depicts an attempted epoxidation of palmarumycin $CP_1$.

Because of the close structural similarity between palmarumycin $CP_1$ and the farnesyl-protein transferase (FTPase) inhibitor deoxypreussomerin A, an epoxidation reaction of palmarumycin $CP_1$ was attempted. However, treatment with hydrogen peroxide anion led to decomposition instead of epoxidation, and a mild epoxidizing agent, dimethyldioxirane also provided only decomposed products. Even after protection of the phenol function of palmarumycin $CP_1$, as the TBDMS ether, no synthetically useful epoxidation could be achieved as shown in FIG. 16. Therefore, the inventors used earlier, more extensively protected synthetic intermediates.

Figure 17:
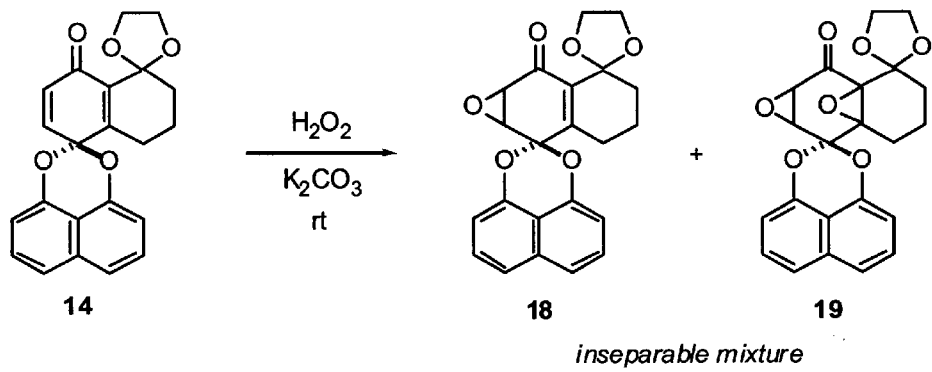
FIG. 17 depicts an attempted epoxidation of 1-oxo-1,4, 5,6,7,8-hexahydronaphthalene-4-spiro-2'-naphtho [1",8"-de][1',3']dioxin-8-spiro-2'''-dioxolane.

When compound 14 was treated with excess hydrogen peroxide anion, as shown in FIG. 17, monitoring of the reaction progress was difficult due to the overlap of products with the starting material 14 on TLC. The reaction mixture was thus quenched before complete consumption of 14. $_1$H NMR analysis of the crude product showed that mono- and diepoxides were formed in a ratio of about 1:1 with ~10% remaining starting material. This result demonstrated that a regioselective epoxidation of the disubstituted double bond of 14 in the presence of the internal tetrasubstituted double bond was unlikely to succeed.

Figure 18:
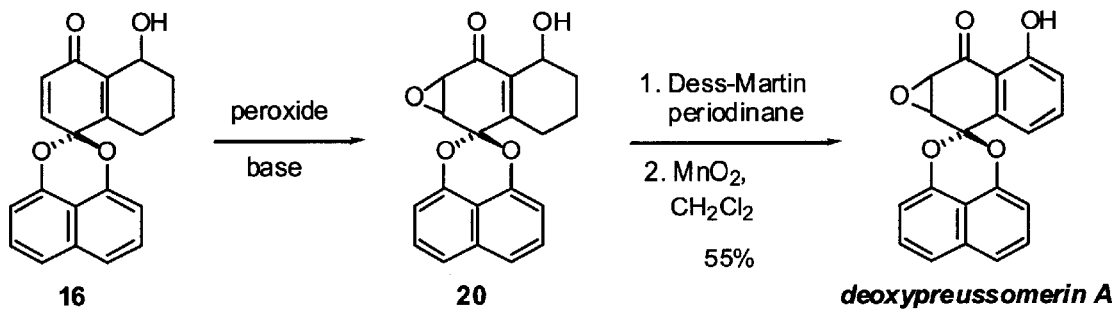
FIG. 18 illustrates treatment of (±)-8-hydroxy-1-oxo-1,4, 5,6,7,8-hexahydronaphthalene-4-spiro-2'-naphtho [1",8"-de][1',3']dioxin with hydrogen peroxide anion.

In contrast, treatment of allylic alcohol 16 with hydrogen peroxide anion resulted in the is olation of the desired monoepoxide 20 in 25% yield as depicted in FIG. 18. The relative configuration of the epoxide and the hydroxyl group was not determined. Peroxides and bases were screened to optimize the epoxidation reaction. When cumene hydroperoxide and NaH were used at −20° C., the epoxidation yield increased to 47%. The two step oxidation protocol developed for the synthesis of palmarumycin $CP_1$ converted epoxy alcohol 20 to the desired natural product in 55% yield. (±)-Deoxypreussomerin A was synthesized in 15% overall yield and 9 steps from the known 8.

TABLE I

| PEROXIDE | BASE | TEMPERATURE | YIELD OF 20 |
|---|---|---|---|
| Hydrogen peroxide | $K_2CO_3$ | rt | 25% |
| t-Butyl hydroperoxide | NaOH | 0° C. | 31% |
| Cumene hydroperoxide | NaOH | 0° C. | 40% |
| Cumene hydroperoxide | NaH | 0° C. | 45% |
| Cumene hydroperoxide | NaH | −20° C. | 47% |

Synthesis of 5-hydroxy-8-methoxy-1,2,3,4-tetrahydronaphthalene-1-spiro-2'-dioxolane (compound 6). To a solution of compound 8 (4.8 g, 25 nimol) and ethylene glycol (3.1 g, 50 mmol) in benzene (700 mL) was added PPTS (0.3 g). The reaction mixture was heated at reflux for 30 hours in a flask equipped with a Dean-Stark apparatus, washed with 5% $NaHCO_3$ solution (2×200 mL) and brine (300 mL), dried ($Na_2SO_4$), and concentrated in vacuo. Chromatography on SiO2 (hexanes/EtOAc, 2: 1) gave 5.32 g (90%) of compound 6 as a solid: Mp 139–140 ° C.; IR (neat) 3359, 2928, 1583, 1468, 1327, 1244, 1159, 1118, 1064, 1008, 945, 924, 864, 794, 716 cm$^{-1}$; $^1$H NMR δ6.55 (d, 1 H, J =8.8 Hz), 6.54 (d, 1 H, J =8.8 Hz), 5.42 (s, 1 H, OH), 4.25 (t, 2 H, J =6.6 Hz), 4.07 (t, 2 H, J =6.6 Hz), 3.75 (s, 3 H), 2.57 (t, 2 H, J =6.0 Hz), 1.93–1.80 (m, 4 H); $^{13}$C NMR δ152.6, 146.9, 128.3, 125.8, 115.2, 110.7, 108.1, 65.5, 56.6, 35.9, 24.0, 20.1; MS (EI) m/z (rel intensity) 236 (M+, 94), 208 (100), 193 (19), 175 (11), 164 (19), 149 (11), 134 (20), 121 (10), 106 (10), 99 (20), 77 (10), 65 (9), 55 (13); HRMS (EI) calcd for $C_{13}H_{16}O_4$ 236.1049, found 236.1052. 10067.

Synthesis of 8-methoxy-5-(8'-methoxynaphthalene-1'-yloxy)-3,4-dihydro-2H-naphthalen-1-one (compound 10). To a solution of compound 6 (4.72 g, 0.02 mol) and 7 (8.52 g, 0.03 mol) in degassed pyridine (150 mL) were added $K_2CO_3$ (2.76 g, 0.02 mol) and $Cu_2O$ (286 mg, 0.002 mol). This reaction mixture was heated at reflux for 12 hours under a nitrogen atmosphere. After addition of additional $Cu_2O$ (286 mg, 0.002 mol) to the solution, heating was continued for 12 h. Pyridine was removed under reduced pressure and the residue was redissolved in EtOAc (300 mL). It was washed with water (100 mL) and brine (100 mL), dried ($Na_2SO_4$), and concentrated in vacuo. Chromatography on $SiO_2$ (hexanes/EtOAc, 2: 1) gave 6.14 g (78%) of compound 9 as an oil. This oil was treated with TsOH (100 mg) in a mixture of acetone/water (7: 1, 50 mL) for 7 hours at room temperature. The reaction mixture was concentrated in vacuo and the residue was diluted with EtOAc (300 mL), washed with water (2×100 mL) and brine (100 mL), dried ($Na_2SO_4$), and concentrated in vacuo. Chromatography on $SiO_2$ (hexanes/EtOAc, 1: 1) gave 5.44 g (100%) of compound 10 as a colorless solid: Mp 152–153 °C; IR(neat) 2952, 1696, 1581, 1484, 1387, 1272, 1245, 1183, 1095, 980, 838, 821, 759 cm$^{-1}$; $^1$H NMR δ7.59 (dd, 1 H, J =8.2, 0.8 Hz), 7.45 (dd, 1 H, J =8.2, 1.0Hz), 7.37 (q, 2 H, J =7.9Hz), 6.87 (dd, 1 H, J =7.6, 0.8 Hz), 6.81 (dd, 1 H, J =7.6, 0.8 Hz), 6.72 (d, 1 H, J=8.9 Hz), 6.67 (d, 1 H, J =9.1 Hz), 3.84 (s, 3 H),3.74 (s, 3 H), 3.05 (t, 2 H, J=6.2 Hz), 2.67 (t, 2 H, J =6.3 Hz), 2.11 (p, 2 H, J =6.4 Hz); $^{13}$C NMR δ197.9, 156.2, 155.4, 152.7, 149.3, 137.6,136.4, 126.7, 126.4, 124.1, 123.1, 121.7, 120.7, 118.8, 115.9, 110.1, 106.1, 56.3, 56.0, 40.9, 24.1, 22.5; MS (EI) m/z (rel intensity) 348 (M+, 100), 319 (7), 305 (10), 291 (14), 261 (8), 218 (7), 189 (12), 174 (24), 158 (45), 127 (34), 115 (29), 101 (10), 77 (15), 63 (8); HRMS (EI) Calcd for $C_{22}H_{20}O_4$ 348.1361, found 348.1361.

Synthesis of 8-hydroxy-5-(8'-hydroxynaphthalen-1'-yloxy)-3,4-dihydro-2H-naphthalen-1-one (compound 11). To a solution of compound 10 (3.92 g, 11.3 mmol) in $CH_2Cl_2$ (120 mL) was added a 1 M solution of $BBr_3$ in $CH_2Cl_2$ (40 mL, 40 mmol) at −78° C. The reaction mixture was warmed to room temperature, stirred for 12 h, poured into ice water (200 g) and extracted with $CH_2Cl_2$ (2×300 mL). The combined organic layers were washed with brine (200 mL), dried ($Na_2SO_4$) and concentrated in vacuo. Chromatography on $SiO_2$ (hexanes/EtOAc, 8:1) gave 3.44 g (95%) of compound 11 as a colorless solid: Mp 165–166° C; IR (neat) 3403, 2947, 1624, 1449, 1387,1343, 1289, 1213, 1167, 1024, 808, 749 cm$^1$; $^1$H NMR δ12.46 (s, 1 H, OH), 9.02 (s, 1 H, OH), 7.50–7.32 (m, 4 H), 7.18 (t, 1 H, J =8.0 Hz), 6.98 (dd, 1 H, J =7.2, 1.1 Hz), 6.93 (d, 1 H, J=8.9 Hz), 6.40 (d, 1 H, J =7.7 Hz), 2.85 (t, 2 H, J =6.0 Hz), 2,70 (t, 2 H, J =6.3 Hz), 2.06 p, 2 H,J=6.4 Hz); $^{13}$C NMR δ204.7, 161.1, 155.4,154.0, 141.8, 137.2, 137.1, 131.1, 128.1, 125.5, 123.1, 119.3, 117.4, 117.1, 114.9, 111.0, 107.4, 38.7,23.6, 22.1;MS (EI) m/z (rel intensity) 320 (M+, 100), 287 (6), 263 (10), 247 (7), 177 (9), 159 (25), 144 (38), 131 (29), 115 (34), 103 (15), 89 (10), 77 (23), 65 (14); HRMS (EI) Calcd for $C_{20}H_{16}O_4$ 320.1049, found 320.1044.

Synthesis of acetic acid 8-(4'-acetoxy-5'-oxo-5',6',7',8'-tetrahydro-naphthalen-1'-yloxy)-naphthalen-1-yl ester (compound 12). To a solution of compound 11 (487 mg, 1.52 mmol) in acetic anhydride (2 mL) was added sodium acetate (100 mg). The reaction mixture was heated to 95° C, stirred for 4 hours and cooled to room temperature. The mixture was poured into ice water (100 g), stirred for 1 hours and extracted with ethyl acetate (100 mL). The ethyl acetate layer was washed with brine (50 mL), dried ($Na_2SO_4$) and concentrated in vacuo. Chromatography on SiO2 (hexanes/EtOAc, 2:1) gave 607 mg (99%) of compound 12 as an oil: IR (neat) 3059, 2951, 1765, 1686, 1601, 1573, 1460, 1367, 1258, 1202, 1115, 1025, 898, 825, 760, 735 cm$^1$; $^1$H NMR δ7.77 (d, 1 H, J =7.9 Hz), 7.58 (d, 1 H, J =8.0 Hz), 7.50 (t, 1 H, J=8.0 Hz), 7.29 (t, 1 H, J=7.7 Hz), 7.18 (t, 1 H, J=7.4 Hz), 7.16 (d, 1 H, J =7.6 Hz), 6.97 (d, 1 H, J=8.7Hz), 6.58 (dd, 1 H, J =7.7, 0.7Hz), 2.91 (t, 2 H, J =5.7 Hz), 2.62 (t, 2 H, J =6.2Hz), 2.40 (s, 3 H), 2.19 (s, 3 H), 2.07 (p, 2 H, J =6.4 Hz); $^{13}$C NMR δ196.3, 170.3, 170.0, 153.1, 150.8, 146.8, 146.0, 138.3, 137.1, 126.6, 126.4, 126.3, 126.2, 125.8, 123.3, 123.1, 120.0, 119.4, 111.8, 40.1, 23.8, 22.0, 21.2, 21.1; MS (EI) m/z (rel intensity) 404 (M+, 23), 362 (30), 320 (100), 202 (10), 149 (21), 115 (12), 91 (33), 69 (18), 57 (28); HRMS (EI) calcd for $C_{24}H_{20}O_6$ 404.1260, found 404.1266.

Synthesis of 8-hydroxy-5-(8'-hydroxynaphthalene-1'-yloxy)-1,2,3,4-tetrahydronaphthalene-1-spiro-2"-dioxolane (compound 13). To a solution of compound 12 (240 mg, 0.593 mmol) and ethylene glycol (1.10 g, 17.79 nunol) in benzene (20 mL) was added PPTS (75 mg, 0.297 mmol). The reaction mixture was heated at reflux for 62 hours in a flask equipped with a Dean-Stark apparatus, cooled to room temperature, diluted with benzene (100 mL), washed with 5% $NaHCO_3$ solution (2×50 mL) and brine (50 mL), dried ($Na_2SO_4$), and concentrated in vacuo. Chromatography on $SiO_2$ (hexanes/EtOAc, 1: 1) gave 205 mg (77%) of compound 13 as an oil. To a solution of compound 13 (175 mg, 0.39 mmol) in degassed THE/MeOH (15 mL, 2/1) was added lithium hydroxide monohydrate (41 mg, 0.98 mmol) at 0 °C. The reaction mixture was stirred for 2 hours in an ice bath, neutralized with saturated ammonium chloride solution and extracted with ethyl acetate (2×100 mL). The combined organic layers were washed with brine (100 mL), dried ($Na_2SO_4$), and concentrated in vacuo. Chromatography on $SiO_2$ (hexanes/EtOAc, 2: 1) gave 137 mg (96%) of compound 5 as a solid: Mp 174–175 °C.; IR (neat) 3405, 3318, 3057. 2959, 2904, 1608, 1581, 1469,1402, 1365, 1301, 1253, 1220, 1182, 1157, 1121, 1035, 944, 928, 878, 818, 759 cm$^{+1}$; $^1$H NMR δ9.18 (s, 1 H, OH), 8.43 (s, 1 H, OH), 7.46–7.34 (m, 3 H), 7.17 (t, 1 H, J =8.0 Hz), 7.10 (d, 1 H, J=8.8 Hz), 6.96 (dd, 1 H, J=7.2, 1.1 Hz), 6.85 (d, 1 H, J=8.8 Hz), 6.45 (d, 1 H, J =7.6 Hz), 4.34–4.17 (m, 4 H), 2.68 (t, 2 H, J=6.3 Hz), 1.99–1.95 (m, 2 H), 1.91–1.83 (m, 2 H); $^{13}$C NMR δ155.5, 154.8, 154.2, 143.3, 137.0, 133.5, 127.8, 125.7, 124.4, 122.6, 120.6, 119.1, 116.1, 114.9, 110.6, 109.8, 107.3, 63.9, 31.3, 23.5, 19.2; MS (EI) m/z (rel intensity) 364(M+, 100), 320 (55), 159 (11), 144 (24), 131 (14), 115 (22), 77 (7), 55 (8); HRMS (EI) calcd for $C_{22}H_{20}O_5$ 364.1311, found 364.1311.

Synthesis of 1-oxo-1,4,5,6,7,8-hexahydronaphthalene-4-spiro-2'-naphtho [1",8"',3']dioxin-8-spiro-2'"-dioxolane (compound 14). To a suspension of compound 5 (58 mg, 0.159 mmol) in trifluoroethanol (20 mL) was added PhI(OAc)$_2$ (62 mg, 0.191 mmol). The reaction mixture was stirred for 2 hours at room temperature and $NaHCO_3$ (32 mg, 0.382 mmol) was added. The resulting mixture was concentrated in vacuo and the residue was diluted with EtOAc (50 mL), washed with water (30 mL) and brine (30 mL), dried ($Na_2SO_4$), and concentrated in vacuo. Chromatography on $SiO_2$ (hexanes/EtOAc, 4:1) gave 43 mg (75%) of compound 14 as an oily solid: IR(neat)3059, 2949,2897, 1680, 1651, 1608, 1584, 1412, 1396, 1302, 1271, 1144, 1096, 1052, 1031, 949, 825, 814, 757 cm$^{-1}$; $^1$H NMR δ7.52 (d, 2 H, J=8.1 Hz), 7.43 (t, 2 H, J =7.9 Hz), 6.93 (d, 2 H, J =7.1 Hz), 6.76 (d, 1 H, J =10.3 Hz), 6.08 (d, 1 H, J =10.4 Hz), 4.41–4.36 (m, 2 H), 4.08-4.04 (m, 2 H), 2.75–2.65 (m, 2 H), 1.95–1.85 (m, 4 H); $^{13}$C NMRδ182.4, 154.1, 146.8, 136.4, 134.1, 134.0, 130.6, 127.6, 121.2, 112.9, 109.7, 105.9, 92.8, 66.1, 35.6, 24.5, 19.5; MS (El) m/z (rel intensity) 362 (M+, 100), 319 (39), 306 (16), 262 (15), 234 (9), 204 (10), 178 (16), 131 (13), 115 (17), 99 (13), 84 (22), 55 (13); HRMS (EI) calcd for $C_{22}H_{18}O_5$ 362.1154, found 362.1160.

Synthesis of (±)-8-hydroxy-1-oxo-1,4,5,6,7,8-hexahydronaphthalene-4-spiro-2'-naphtho [1",8"-de][1',3'] dioxin (compound 16). To a solution of compound 11 (1.51 g, 4.72 nmmol) in Et$_2$O (70 nmL) was added in portions solid LiAlH4 (358 mg, 9.44 mmol) at 0 °C. The solution was stirred for 2 hours at 0 °C, warmed to room temperature and stirred for an additional 2 hours. The reaction mixture was carefully quenched with 5% sodium bisulfate solution in an ice bath. After adding 40 mL of 5% sodium bisulfate solution, the product was extracted with Et$_2$O (2×150 mL). The combined ether layers were washed with brine (100 mL), dried ($Na_2SO_4$) and concentrated in vacuo. The resulting solid was added to dry trifluoroethanol (150 mL) and stirred until a fmie suspension was obtained. After addition of PhI(OAc)$_2$ (1.67 g, 5.19 mmol), the mixture was stirred for 30 min at room temperature, NaHCO$_3$ (1.0 g, 12 mmol) was added. The solution was concentrated in vacuo and the resulting residue was diluted with EtOAc (300 mL), washed with water (100 mL) and brine (100 nmL), dried (Na2SO4), and concentrated in vacuo. Chromatography on SiO2 (hexanes/EtOAc, 2:1) gave 1.32 g (87%) of compound 16 as a yellow solid: Mp 199–200 °C; IR (neat) 3434, 2945, 1673, 1642,1630,1600, 1409, 1374,1263, 1080, 944, 757 cm$^{-1}$; $^1$HNMR δ7.54 (d, 2 H, J =8.0 Hz), 7.45 (td, 2 H, J =7.4, 2.2 Hz), 6.95 (td, 2 H, J =7.6, 0.7 Hz), 6.90 (d, 1 H, J =10.4 Hz), 6.19 (d, 1 H, J =10.4 Hz), 4.82 (t, 1 H, J =4.9 Hz), 3.31 (bs, 1 H, OH), 2.78–2.51 (m, 2 H), 1.98–1.90 (m, 3 H), 1.82–1.72 (m, 1 H); $^{13}$C NMRδ185.8, 151.6, 146.8, 139.3, 135.6, 134.1, 129.1, 127.7, 127.6, 121.3, 112.9, 109.8, 109.7, 92.6, 62.7, 29.6, 24.2, 17.7; MS (El) mn/z (rel intensity) 320 (M+, 100), 304 (30), 265 (35), 247 (21), 235 (10), 219 (11), 197 (18), 169 (24), 160 (32), 144 (35), 133 (35), 115 (50), 103 (16), 88 (13), 77 (28), 63 (17); HRMS (EI) Calcd for C$_{20}$H$_{16}$O$_4$ 320.1049, found 320.1039

Synthesis of 8-hydroxy-1-oxo-1,4-dihydronaphthalene-4-spiro-2'-naphtho[1",8"-de] [1',3'] dioxin (palmarumycin CP,). To a solution of compound 16 (32 mg, 0.1 mmol) in CH$_2$Cl$_2$ (5 mL) was added Dess-Martin periodinane (64 mg, 0.15 mmol) at room temperature. The reaction mixture was stirred for 2 hours and diluted with EtOAc (30 mL). It was washed with 5% NaHCO$_3$ solution (10 mL) and brine (15 mL), dried (Na$_2$SO$_4$), and concentrated in vacuo. Chromatography on SiO$_2$ (hexanes/EtOAc, 2:1) gave 32 mg of a yellow residue which was treated with MnO$_2$ (Aldrich, 85% activated, 102 mg, 1 mnmol, dried over P$_2$O$_5$ just before use) in dry CH$_2$Cl$_2$ (5 mL) for 2 days at room temperature. The reaction mixture was filtered through celite and washed with CH$_2$Cl$_2$ (10 mnL). The combined solutions were concentrated in vacuo. Chromatography on SiO$_2$ (hexanes/EtOAc, 4: 1) gave 19 mg (60%) of palmarumycin CPI as a yellow solid; Mp 170 °C (dec.); IR (neat) 3053, 1659, 1602, 1449, 1409, 1372, 1341, 1269, 1237, 1110, 1073, 942, 822, 746 cm$^1$; 'HNMR 12.17 (s, 1 H, OH), 7.67 (t, 1 H,J =8.0 Hz), 7.58 (d, 2 H, J =8.5 Hz), 7.47 (t, 2 H, J=7.9 Hz), 7.46 (d, 1 H, J=7.8 Hz), 7.14 (dd, 1 H, J=8.2, 1.1 Hz), 7.02 (d, 1 H, J=10.9 Hz), 6.98 (d, 2 H, J=7.7 Hz), 6.37 (d, 1 H, J=10.9 Hz); $^{13}$C NMR δ188.8, 161.9, 147.2, 139.7, 138.8, 136.7, 134.2, 129.8, 127.7, 121.4, 119.7, 119.4, 113.8, 113.0, 109.9, 92.9; MS (El) m/z (rel intensity) 316 (M+, 100), 288 (12), 287 (19), 259 (8), 175 (11), 114 (45), 88 (11), 63 (9); HRMS (EI) Calcd for C$_{20}$H$_{12}$O$_4$ 316.0736, found 316.0730.

Synthesis of (+)-2,3-epoxy-8-hydroxy-1-oxo-1,2,3,4-tetrahydro-naphthalene-4-spiro-2'-naphtho [1",8"-de][1',3'] dioxin [(+)-deoxypreussomerin A]. To a solution of compound 16 (54.5 mg, 0.17 mmol) in THF (5 mL) was added cumene hydroperoxide (157 gL, 0.85 mmol) and NaH (60%, 6.5 mg, 0.17 mmol) at -20 °C. The reaction mixture was stirred for 4 hours at -20 °C, and diluted with EtOAc (40 mL) and brine (5 mL). The separated organic layer was washed with an additional brine (20 mL), dried (Na$_2$SO$_4$), and concentrated in vacuo. Chromatography on SiO$_2$ (hexanes/EtOAc, 3:1) gave 27 mg (47%/o) of monoepoxide 20. To a solution of this epoxide in CH$_2$Cl$_2$ (4 mL) was added Dess-Martin periodinane (51 mg, 0.12 mmol) at room temperature. The reaction mixture was stirred for 2 hours, diluted with EtOAc (30 mL), washed with 5% NaHCO$_3$ solution (10 niL) and brine (15 mL), dried (Na$_2$SO$_4$), and concentrated in vacuo. Chromatography on SiO$_2$ (hexanes/ EtOAc, 2:1) gave 27 mg of a yellow residue which was treated with MnO$_2$ (Aldrich, 85% activated, 82 mg, 0.8 mmol, dried over P$_2$O$_5$ just before use) in dry CH$_2$Cl$_2$ (5 mL) for 37 hours at room temperature. The mixture was filtered through celite and washed with CH$_2$Cl$_2$ (10 mL). The combined solutions were concentrated in vacuo. Chromatography on SiO$_2$ (hexanes/EtOAc, 3:1) gave 14.5 mg (26% from compound 16) of (+)-deoxypreussomerin A as a colorless solid: Mp 200–201 °C; IR (neat) 3050, 1651, 1605, 1455, 1409, 1380, 1330, 1266, 1239, 1173, 1110, 1061, 963, 920, 878, 820, 809, 759, 720 cm$^{-1}$; $^1$HNMR δ11.37 (s, 1 H, OH), 7.65 (t, 1 H, J =8.0 Hz), 7.60 (d, 1 H, J =8.6 Hz), 7.57 (d, 1 H, J =8.0 Hz), 7.53 (t, 1 H, J =8.3 Hz), 7.45 (t, 1 H, J =7.4 Hz), 7.44 (d, 1 H, J =7.9 Hz), 7.19 (dd, 1 H, J =7.6, 0.8 Hz), 7.14 (dd, 1 H, J =8.6, 0.8 Hz), 6.92 (dd, 1 H, J =7.6, 0.7 Hz), 4.09 (d, 1 H, J =4.1 Hz), 3.68 (d, 1 H, J =3.9 Hz); $^{13}$C NMR δ196.6, 161.9, 146.9, 146.7, 137.8, 136.9, 134.2, 127.9,127.7, 121.5, 121.4, 120.1, 119.1, 112.8, 112.3,110.2, 109.4, 96.0,53.3; MS (El) m/z (rel intensity) 332 (M+, 100), 316 (28), 303 (11), 287 (19), 173 (15), 145 (23), 132 (12), 114 (27), 89 (13), 74 (14), 63 (12), 57 (7); HRMS(EI) Calcd for C$_{20}$H$_{12}$O$_5$ 332.0685, found 332.0688.

Example 2 - Synthesis of (E)-8-(3-phenyl-allyloxy)-1-oxo-1,4-dihydronaphthalene-4-spiro-2'-naphto[1", 8"-de][1',3'] dioxin (compound 21). General procedure for Mitsunobu reactions. A solution of palmarumycin CPI (7.4 mg, 0.023 mmol), diphenylphosphino-polystyrene (82.1 mg, 1.41 mnmol/g, 0.116 mmol) and cinnamyl alcohol (15.5 laL, 0.118 mmol) in dry CH$_2$Cl$_2$ (0.4 mL) was stirred for 30 min at room temperature and cooled to 0 °C. Diethyl azodicarboxylate (DEAD) (18.0 μL, 0.114 mmol) was added to the reaction mixture at 0 °C and stirring was continued for 24 hours at room temperature. The reaction mixture was washed with 5% aqueous KOH solution (0.5 mL), followed by 5% HCl (0.5 mL). The methylene chloride extract was filtered, the resin was washed further with CH$_2$Cl$_2$ (2×0.5 mL) and the solvent was concentrated. Chromatography on SiO$_2$ (hexanes/EtOAc, 9:1) gave 1.8 mg (24%) of palmarumycin CPI and 5.0 mg (52%) of 21 as a colorless oil: $^1$H NMR δ7.70 (t, 1 H, J =8.0 Hz), 7.60–7.56 (m, 3 H), 7.50–7.45 (m, 4 H), 7.37–7.20 (m, 4 ),6.99 (d, 2 H, J =7.3 Hz), 6.93 (bs, 1 H), 6.87 (d, 1 H, J =10.5 Hz), 6.49 (dt, 1 H, J =5.2, 16.0 Hz), 6.31 (d, 1 H, J =10.5 Hz), 4.93 (d, 2 H, J =5.2 Hz); HRMS(EI) Calcd for C$_{29}$H$_{20}$O$_4$ 432.1362, found 432.1362.

Example 3 - Synthesis of (E)-8-(but-2-enyloxy)-1-oxo-1, 4-dihydronaphthalene-4-spiro-2'-napthto [1",8"-de][1',3'] dioxin (compound 22). According to the general procedure, palmarumycin CPI (2.4 mg, 0.008 mmol), diphenylphosphino-polystyrene (28.2 mg, 1.41 mmol/g, 0.040 mmol), 2-buten-1-ol (3.3 pμL, 0.038 mnmol) and DEAD (6.0 liL, 0.038 mmol) in dry CH$_2$Cl$_2$ (0.2 mL) provided after 24 hours 2.5 mg (88%) of 22 as a colorless oil: $^1$H NMR δ7.68 (t, 1 H, J =8.0 Hz), 7.60–7.55 (m, 3 H), 7.49 (d, 1 H, J =7.7 Hz), 7.46 (d, 1 H, J =8.2 Hz), 7.17 (d, 1 H, J =8.6 Hz), 6.98 (d, 2 H, J =7.4 Hz), 6.85 (d, 1 H, J =10.5 Hz), 6.29 (d, 1 H, J =10.5 Hz), 6.03 (dq, 1 H, J =15.3, 6.5 Hz), 5.85–5.75 (m, 1 H), 4.69 (d, 2 H, J =5.4 Hz), 1.80 (d, 3 H, J =6.2 Hz); HRMS(EI) Calcd for C$_{24}$H$_{18}$O$_4$ 370.1205, found 370.1214.

Example 4 - Synthesis of 8-hexyloxy-1-oxo-1,4-dihydronaphthalene-4-spiro-2'-napthto [1",8"-de] [1',3'] dioxin (compound 23). According to the general procedure, palmarumycin CP$_1$ (2.0 mg, 0.006 mmol), diphenylphosphino-polystyrene (31.3 mg, 1.41 mmol/g, 0.044 mmol), hexyl alcohol (4.0 μL, 0.031 mmol) and DEAD (5.0 μL, 0.032 mmol) in dry CH$_2$Cl$_2$ (0.1 mL) provided after 43 hours 1.3 mg (50%/o) of 23 as a colorless oil: $^1$H NMR δ7.66 (t, 1 H, J =8.3 Hz), 7.57–7.50 (m, 3 H), 7.48–7.42 (m, 2 H), 7.14 (d, 1 H, J =8.3 Hz), 6.96 (d, 2 H, J=7.5 Hz), 6.82 (d, 1 H,J=10.4 Hz), 6.26 (d, 1 H, J =10.4 Hz), 4.10 (t, 2 H, J=5.9 Hz), 2.30–1.20 (m, 11 H).

Example 5 - Synthesis of (E)-8-(hex-3-enyloxy)-1-oxo-1,4-dihydronaphthalene-4-spiro-2'-naphto [1",8"-de][1',3'] dioxin (compound 24, SR-4). According to the general procedure, palmarumycin $CP_1$ (2.1 mg, 0.007 mmol), diphenylphosphino-polystyrene (23.9 mg, 1.41 mmol/g, 0.034 mmol), trans-3-hexen-1-ol (4.2 μL, 0.034 mmol) and DEAD (5.2 μL, 0.033 mmol) in dry $CH_2Cl_2$ (0.1 mL) provided after 67 hours 1.3 mg (43%) of 24 as a colorless oil: $^1$H NMR δ 7.68 (t, 1 H, J =8.3 Hz), 7.60–7.45 (m, 5 H), 7.16 (d, 1 H, J =8.4 Hz), 6.97 (d, 2 H, J =7.5 Hz), 6.85 (d, 1 H, J =10.5 Hz), 6.28 (d, 1 H, J=10.4 Hz), 5.66–5.60 (m, 1 H), 5.45–5.30 (m, 1 H), 4.15 (t, 2 H, J =6.9 Hz), 2.7–2.6 (m, 2 H), 2.4–2.3 (m, 2 H), 1.00 (t, 3 H, J =6.4 Hz).

Example 6 - Synthesis of 8-(3-methoxy-benzyloxy)-1-oxo-1,4-dihydronaphthalene-4-spiro-2'-naphto [1",8"-de][1',3'] dioxin (compound 25). According to the general procedure, palmarumycin $CP_1$ (2.0 mg, 0.006 mmol), diphenylphosphino-polystyrene (22.8 mg, 1.41 mmol/g, 0.032 mmol), 3-mehoxybenzyl alcohol (4.0 μL, 0.032 mmol) and DEAD (5.0 niL, 0.032 mmol) in dry $CH_2Cl_2$ (0.1 mL) provided after 45 hours 1.6 mg (67%) of 25 as a colorless oil: $^1$H NMR δ7.68–7.54 (m, 4 H), 7.45 (t, 2 H, J =7.7 Hz), 7.24–7.10 (m, 4 H), 6.97 (d, 2 H, J =7.5 Hz), 6.9–6.8 (m, 2 H), 6.30 (d, 1 H, J =10.4 Hz), 5.29 (s, 2 H), 3.86 (s, 3 H).

Example 7 - Synthesis of 8-(2-phenyl-ethoxy)-1-oxo-1,4-dihydronaphthalene-4-spiro-2'-naphto [1",8"-de][1',3'] dioxin (compound 26). According to the general procedure, palmarumycin CP, (2.0 mg, 0.006 mmol), diphenylphosphino-polystyrene (23.4 mg, 1.41 mmol/g, 0.033 nmmol), phenethyl alcohol (3.8,μL, 0.032 nmmol) and DEAD (5.0,μL, 0.032 nmmol) in dry $CH_2Cl_2$ (0.2 mL) provided after 24 hours 1.0 mg (33%) of 26 as a colorless oil: $^1$H NMR δ7.67–7.1 (m, 12 H), 6.98 (d, 2 H, J =7.5 Hz), 6.86 (d, 1 H, J =10.5 Hz), 6.30 (d, 1 H, J =10.6 Hz), 4.33 (t, 2 H, J =7.0 Hz), 3.27 (t, 2 H, J =7.0 Hz).

Example 8 - Synthesis of 8-(furan-2-ylmethoxy)-1-oxo-1,4-dihydronaphthalene-4-spiro-2'-naphto [1",8"-de][1',3'] dioxin (compound 27) (SR-7) and 7-(furan-2-ylmethyl)-8-hydroxy-1-oxo-1,4-dihydronaphthalene-4-spiro-2'-naphto [1",8"-de] [1',3 '] dioxin (compound 28). According to the general procedure, palmarumycin $CP_1$ (2.1 mg, 0.007 mmol), diphenylphosphino-polystyrene (22.5 mg, 1.41 mmol/g, 0.032 mmol), furfuryl alcohol (2.8,μL, 0.032 mmol) and DEAD (5.0 μL, 0.032 mmol) in dry $CH_2Cl_2$ (0.2 mL) provided after 5 d 2.0 mg (71%) of 27 and 1.0 mg (29%) of 28 as colorless oils. 27: $^1$H NMR δ7.70–7.45 (m, 6 H), 7.29–7.26 (m, 2 H), 7.05–6.95 (m, 2 H), 6.86 (d, 1 H, J =10.5 Hz), 6.55 (bs, 1 H), 6.41 (bs, 1 H), 6.28 (d, 1 H, J=10.5 Hz), 5.23 (s, 2 H). 28: $^1$H NMR β12.67 (s, 1 H), 7.61 (d, 2 H, J =8.2 Hz), 7.62–7.44 (m, 4 H), 7.11 (d, 1 H =8.8 Hz), 7.00–6.92 (m, 3 H), 6.35 (d, 1 H =10.4 Hz), 6.26 (t, 1 H, J =2.4 Hz), 5.91 (d, 1 H, J =3.2 Hz), 4.26 (s, 2 H).

Example 9 - Synthesis of (E,E)-8-(3,7-diemthyl-octa-2,6-dienyloxy)-1-oxo-1,4-dihydronaphthalene-4-spiro-2'-naphtol [1",8"-de][1',3'] dioxin (compound 29). According to the general procedure, palmarumycin $CP_1$ (2.0 mg, 0.006 mmol), diphenylphosphino-polystyrene (23.1 mg, 1.41 mmol/g, 0.033 mmol), geraniol (5.6, μL, 0.032 mmol) and DEAD (5.0 μL, 0.032 mmol) in dry $CH_2Cl_2$ (0.2 mL) provided after 29 hours 2.1 mg (83%) of 29 as a colorless oil: $^1$H NMR δ7.67 (t, 1 H, J =8.2 Hz), 7.59–7.55 (m, 3 H), 7.50–7.44 (m, 2 H), 7.16 (d, 1 H, J =8.2 Hz), 6.98 (d, 2 H, J =7.4 Hz), 6.85 (d, 1 H, J =10.5 Hz), 6.28 (d, 1 H, J =10.5 Hz), 5.56 (t, 1 H, J =6.0 Hz), 5.10 (bs, 1 H), 4.79 (d, 2 H, J =6.2 Hz), 2.11 (bs, 4 H), 1.78 (s, 3 H), 1.69 (s, 3 H), 1.62 (s, 3 H).

Example 10 - Synthesis of 8-(furan-3-ylmethoxy)-1-oxo-1,4-dihydronaphthalene-4-spiro-2'-naphto [1',8'-de][1',3'] dioxin (compound 30, SR-10). According to the general procedure, palmarumycin $CP_1$ (2.0 mg, 0.006 mmol), diphenylphosphino-polystyrene (23.4 mg, 1.41 mmol/g, 0.033 mmol), 3-furamnethanol (2.8,μL, 0.032 mmol) and DEAD (5.0 μL, 0.032 mmol) in dry $CH_2Cl_2$ (0.2 mL) provided after 3 d 1.2 mg (50%) of 30 as a colorless oil: $^1$H NMR δ7.63–7.45 (m, 5 H), 7.42–7.35 (m, 3 H), 7.16 (d, 1 H, J=8.2 Hz), 6.89 (d, 2 H, J=7.4 Hz), 6.77 (dd, 1 H, J=10.5, 1.3 Hz), 6.51 (bs, 1 H), 6.20 (dd, 1 H, 3=10.5, 1.3 Hz), 5.08 (s, 2 H); HRMS(EI) Calcd for $C_{25}H_{16}O_5$ 396.0998, found 396.0997.

Example 11 - Synthesis of 8-(pyridin-2-ylmethoxy)-1-oxo-1,4-dihydronaphthalene-4-spiro-2'-naphto [1",8"-de][1',3'] dioxin (compound 31). According to the general procedure, palmarumycin $CP_1$ (2.2 mg, 0.007 mmol), diphenylphosphino-polystyrene (29.7 mg, 1.41 mmol/g, 0.042 rnmol), 2-pyridylcarbinol (3.4 μL, 0.035 rnmol) and DEAD (5.5 μL, 0.035 mmol) in dry $CH_2Cl_2$ (0.2 mL) provided after 4 d 0.2 mg (9%) of palmarumycin $CP_1$ and 1.2 mg (43%) of 31 as a colorless oil: $^1$H NMR δ8.50 (bs, 1 H), 8.16 (bs, 1 H), 7.88 (bs, 1 H), 7.77–7.50 (m, 4 H), 7.51–7.45 (m, 3 H), 7.4–7.3 (m, 1 H); 6.99 (d, 2 H, J =7.7 Hz), 6.92 (bd, 1 H, J =10.5 Hz), 6.33 (d, 1 H, J =10.5 Hz), 5.42 (bs, 2 H); HRMS(EI) Calcd for $C_{26}H_{17}NO_4$ 407.1158, found 407.1139.

Example 12 - Synthesis of 8-(pyridin-3-ylmethoxy)-1-oxo-1,4-dihydronaphthalene-4-spiro-2'-naphto [1",8"-de][1',3'] dioxin (compound 32). According to the general procedure, palmarumycin $CP_1$ (2.1 mg, 0.007 mmol), diphenylphosphino-polystyrene (23.8 mg, 1.41 mmol/g, 0.034 mmol), 3-pyridylcarbinol (3.3 μL, 0.033 numol) and DEAD (5.2 μL, 0.033 mmol) in dry $CH_2Cl_2$ (0.2 mL) provided after 5 d 0.3 mg (14%) of palmarumycin $CP_1$, and 0.9 mg (29%) of 32 as a colorless oil: $^1$H NMR δ8.8–8.5 (m, 2 H), 8.29 (d, 1 H, J =7.9 Hz), 7.74–7.40 (m, 8 H), 7.25–7.20 (m, 1 H), 6.97 (d, 1 H, J =7.1 Hz), 6.88 (d, 1 H, J =10.5 Hz), 6.30 (d, 1 H, J =10.4 Hz), 5.32 (s, 2 H); HRMS(EI) Calcd for $C_{26}H_{17}NO_4$ 407.1158, found 407.1152.

Example 13 - Synthesis of 8-(pyridin-4-ylmethoxy)-1-oxo-1,4-dihydronaphthalene-4-spiro-2'-naphtol [1",8"-de][1',3'] dioxin (compound 33). According to the general procedure, palmarumycin $CP_1$ (2.0 mg, 0.006 mmol), diphenylphosphino-polystyrene (22.4 mg, 1.41 mmol/g, 0.032 mmol), 4-pyridylcarbinol (7.6 mg, 0.069 mmol) and DEAD (5.0 μL, 0.032 mmol) in dry $CH_2Cl_2$ (0.2 mL) provided after 7 d 0.6 mg (30%) of palmarumycin $CP_1$ and 0.5 mg (17%) of 33 as a colorless oil: $^1$H NMR δ8.9–8.5 (m, 2 H), 8.10 (bs, 1 H), 7.78–7.1 (m, 7 H), 7.00 (d, 2 H, J =7.4 Hz), 6.94 (d, 1 H, J =10.5 Hz), 6.34 (d, 1 H, J =10.5 Hz), 5.40 (bs,1 H), 4.80 (bs, 2 H).

Example 14 - Synthesis of 8-allyloxy-1-oxo-1,4-dihydronaphthalene-4-spiro-2'-naphto [1",8"-de][1',3'] dioxin (compound 34). According to the general procedure, palmarumycin $CP_1$(2.1 mg, 0.007 mmol), diphenylphosphino-polystyrene (23.5 mg, 1.41 mmol/g, 0.033 mmol), allyl alcohol (2.3 μL, 0.034 mmol) and DEAD (5.2 μL, 0.033 mmol) in dry $CH_2Cl_2$ (0.2 mL) provided after 3 d 0.6 mg (33%) of palmarumycin $CP_1$ and 1.8 mg (71%) of 34 as a colorless oil: $^1$H NMR δ7.69 (t, 1 H, J =8.1 Hz), 7.62–7.56 (m, 2 H), 7.49 (d, 1 H, J=7.5 Hz), 7.46 (d, 1 H, J =8.3 Hz), 7.17 (d, 1 H, J =8.3 Hz), 6.98 (d, 2 H, J =7.0 Hz), 6.86 (d, 1 H, J =10.5 Hz), 6.29 (d, 1 H, J =10.7 Hz), 6.20–6.06 (m, 1 H), 5.68 (dd, 1 H, J=17.2, 1.5 Hz), 5.38 (dd, 1 H, J =10.8, 1.5 Hz), 4.77-4.74 (m, 2 H); HRMS(EI) Calcd for $C_{23}H_{16}O_4$ 356.1049, found 356.1064.

Example 15 8-(4-methoxy-benzyloxy)-1-oxo-1,4-dihydronaphthalene4-spiro-2 -naphto [1,8 -de][1, 3 ]dioxin (TH-39).A solution of palmarumycin $CP_1$ (20.1 mg,0.0635 mmol), diphenylphosphino-polystyrene (230 mg, 1.41 mmol/g,0.230 mmol) and 4-methoxybenzyl alcohol (39.6 μL,0.318 mmol) in dry $CH_2Cl_2$ (2 mL) was stirred for 45 min at room temperature and cooled to 0° C. Then DEAD (50 0 μL 0 318 mmol) was added dropwise to the reaction mixture to 0 ° C. The solution was warmed to room temperature, stirred for 35 hours, diluted with additional $CH_2Cl_2$, and washed with 5% aqueous KOH solution followed by 5% HCl. The organic extracts were filtered. The resin was washed further with $CH_2Cl_2$ and the combined extracts were concentrated in vacuo. Chromatography on SiO2 (Hexanes/EtOAc,25:1→10:1→4:1)gave 6.1 mg (69%) of TH-39 :1 H NMR (CDC13)δ7.70–7.45 (m,8H),7.21 (dd,1 H, J=8.1,0.8 Hz),6.98 (t,4 H, J=8.2 Hz),6.87 (d,1 H, J=10.5 Hz),6.31 (d,1H, J=10.5 Hz),5.26 (s,2 H),3.84 (s,3 H);[13] ; C NMR $(CDCl_3)$δ182.7, 159.2, 158.8, 147.4, 141.0, 135.1, 134.7, 134.1, 132.2, 128.4, 128.3, 127.6, 121.2, 120.4, 115.9, 114.1, 109.8, 93.4,70.7,55.3;HRMS (EI) calcd for $C_{28}H_{20}O_5$436.1311, found 436.1323.

Example 16 TH-169 was prepared by hypervalent iodine oxidation as illustrated in FIG. 22A followed by transketalization with ethylene glycol and 2-step aromatization. Spectroscopic data for TH-169.- Mp 96.2–100.5 ° C.;IR (neat) 2956,2919,2852,1662,1617,1460,1393, 1344, 1296, 1240, 1157, 1083,9 67, 843, 806, 746 cm −1; $^1H$ NMR $(CDCl_3)$ δ12.16 (s,1 H),7.54 (t,1 H, J=8.7 Hz),7.12 (d,1 H, J=7.6 Hz),7.01 (d,1 H, J=8.3 Hz),6.85 (d,1 H,J=10.3 Hz),6.33 (d,1 H, J=10.3 Hz),4.4–4.2 (m,4 H); $^{13}C$ NMR $(CDCl_3)$δ189.6, 161.8, 144.1, 141.4, 136.2, 128.3, 118.9, 118.0, 114.6, 99.9, 65.9; HRMS (El) calcd for $C_{12}H_{10}O_4$ 218.0579, found 218.0571.

Figure 19B:
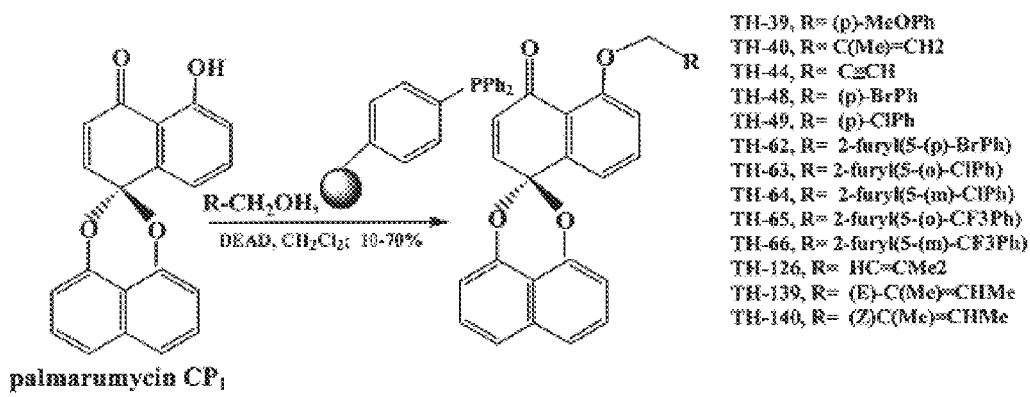

Example 17 For the preparation of TH-223,the cesium salt of diol as illustrated in FIG. 22B was alkylated and cyclized under oxidative conditions. Spectroscopic data for TH-223: Mp 147.5–152.1 ° C.; IR (neat) 2960, 2919, 2840, 1670, 1636, 1595,1475, 1322,1258,1281,1094,1060 cm −1;$^1H$ NMR $(CDCl_3)$δ7.69–7.55 (m,3 H),7.03 (dd,1H,J=7.8,1.5 Hz),6.37 (d,1H, J=10.8 Hz),4.33 (td,2 H, J=12.6,2.5 Hz), 4.09 (dd,2 H, J=7.2,4.6 Hz),3.95 (s,3H),2.5–2.2 (m,1H), 1.65–1.60 (m,1H); $^{13}$ C NMR $(CDCl_3)$δ183.4, 159.4, 145.0, 134.6, 134.5, 130.9, 119.3, 118.6, 112.5, 90.8, 61.3, 56.2, 25.1;HRMS (EI) calcd for $C_{14}H_{14}O_4$ 246.0892, found 246.0896. Biological Assays of Analogs The successful development of efficient synthetic strategies for the preparation of palmarumycin $CP_1$ and deoxypreussomerin A allowed the inventors to prepare analogs and investigate the biological structure-activity relationship (SAR) of these compounds in more detail. The small library of palmarnmycin analogs was obtained by Mitsunobu reaction of the natural product using polystyrene-bound triphenylphosphine and is shown in FIG. 19. A total of 13 allylic and benzylic alcohols were used for the coupling, and yields and ease of purification were greatly improved by the use of the polymer-bound reagent. In the treatment of palmarumycin $CP_1$, with 2-furyl methanol, the ether product 28 was accompanied by the C-alkylated phenol 27 as illustrated in FIG. 20. All other reactions produced a single isomer. The TH-39 through TH-140 series of analogs was prepared in a similar fashion in 10–70% yield from synthetic palmarumycin $CP_1$(FIG. 19B). In addition to these palmarumycin analogs, several diepoxin a derivatives as shown in FIG. 21 were also subjected to biological testing.

All moisture-sensitive reactions were performed under an atmosphere of $N_2$ or Ar and all glassware was dried in an oven at 140 ° C. prior to use. THF and $Et_2O$ were dried by distillation over Na / benzophenone under a nitrogen atmosphere. Dry $CH_2Cl_2$ was obtained by distillation from $CaH_2$. Dry DMF was obtained by distillation from alumina under reduced pressure. Dry $CF_3CH_2OH$ was obtained by distillation from $CaSO_4$. Unless otherwise noted, solvents or reagents were used without further purification. NMR spectra were recorded at either 300 MHz / 75 MHz ($^1H$ / $^{13}C$ NMR) or 500 MHz / 125 MHz ($^1H$ / $^{13}C$ NMR) in $CDCl_3$ unless stated otherwise.

Antiproliferative assay

Two widely used human breast cancer cell lines were evaluated for sensitivity to the cytotoxic effects of the naphthoquinone spiroketals. MCF-7 cells were originally derived from an adenocarcinoma of the breast and retain several characteristics of differentiated mamnmary epithelium including the ability to process estradiol via cytoplasmic estrogen receptors. MCF-7 cells express the tumor suppressor gene product p53, which is required for the programmed cell death or apoptosis caused by many agents. (Foster, B. A.; Coffey, H. A.; Morin, M. J.; Rastinejad, F. *Science* 1999, 286, 2507).

MDA-MB-231 cells, which were also derived from an adenocarcinoma of the breast, are less differentiated than the MCF-7 cells and fail to express functional p53 or estrogen receptors. This class of tumor cells contains important targets for new therapies, because loss of estrogen receptor expression is associated with poor patient prognosis. (Osborne, C. K. *Breast Cane. Res. Treatm.* 1998, 51, 227).

All cells were tested for 72 hours with six concentrations of compounds ranging from 0.1 to 30 μM to determine the concentration required for 50% growth inhibition ($IC_{50}$). The inventors extrapolated to determine the $IC_{50}$ for compounds with little cytotoxicity at 30,μM, the highest concentration tested. As can be appreciated by reference to Table II, 45% of the compounds (10/22) had an $IC_{50}$<3,μM in both cell types. Half of the compounds showed no selectivity to either human tumor cell type, while 32% of the compounds were more cytotoxic to MCF-7 compared with MDA-MB-231 cells. This included compound 37, which was 5-fold more cytotoxic to MCF-7 cells ($IC_{50}$ 4.6 vs. 23 μM). The enhanced sensitivity of MCF-7 to these compounds may be due to the expression of p53 in these cells. The assay used in these studies, however, did not specifically measure apoptosis. At least one compound, 27, can arrest mammalian cells in the G2/M phase of the cell cycle. The five fold enhanced sensitivity of MDA-MB-231 cells to 24 compared to MCF-7 cells is of interest, because the MDA-MB-231 cells lack both functional estrogen receptors and p53.

Thioredoxin reductase assay

Thioredoxin reductase was purified from human placenta as previously described (Oblong, J.E.; Gasdaska, P.Y.; Sherrill, K.; Powis,G. *Biochemistry* 1993, 32, 7271) and recombinant human Trx-1 was prepared as previously described (Gasdaska, P.Y.; Oblong, J.E.; Cotgreave, I.A.; Powis,G. *Biochem.Biophys.Acta* 1994 ,1218 ,292). TrxR and Trx-1/TrxR activities were measured spectrophotometrically using previously published microtiter plate colorimetric assays, based on the increase in absorbance at 405 nm which occurs as dithionitrobenzoic acid (DTNB) is reduced by the enzyme-mediated transfer of reducing equivalents from NADPH (Gasdaska et al., *Biochem.Biophys.Acta* 1994 ,1218,292). Trx-1/TrxR-dependent insulin reducing activity was measured in an incubation with a final volume of 60 μL containing 100 mM HEPES buffer, pH 7.2,5 mM EDTA (HE buffer),1 mM NADPH, 10 μM TrxR,0.8 μM Trx-1 and 2.5 mg/mL bovine insulin. Incubations were for 30 min at 37° C. in flat-bottom 96-well microtiter plates. The reaction was stopped by the addition of 100 μL of 6 M guanidine-HCl, 50 mM Tris, pH 8.0, and 10 mM DTNB, and the absorbance measured to 405 nm. TrxR activity was measured in a final incubation volume of 60 μL containing HE buffer, 10 mM DTNB, 1.0 μM TrxR and 1 mM NADPH. Compounds were diluted in HE buffer and added to the wells as 20 μL aliquots, and TrxR was then added,also as 20 μL aliquots in HE buffer. To start the reaction NADPH and DTNB were added as a 20 μL aliquot in HE buffer and the plate was moved to the plate reader which had been preheated to 37° C. The optical density at 405 nm was measured every 10 s and initial reaction rates were measured.

Table II summarizes Trx-1/TrxR assay data as well as growth inhibition values for selected compounds. The most active compounds inhibited Trx-1/TrxR with IC50 values from 0.35 to low micromolar. In particular, palmarumycin $CP_1$ rivaled the most active known inhibitor of the thioredoxin system, pleurotin, in activity. Palmarumycin $CP_1$ also demonstrated considerable (>30 fold) selectivity for Trx-1 over TrxR. Alkylation at the phenol as shown in the SR-series of analogs mostly abolished activity, with the exception of SR-10,a 3-furylmethyl derivative, and SR-14, an allylated phenol which were nonetheless >50 fold less active. For the most part, this trend is continued in the TH-series, but several derivatives show more significant affinity to the thioredoxin—thioredoxin reductase system. Specifically,TH-40,TH-44,and TH-62 have $IC_{50}$ values from 4.8 to 13.4 μM. The former two are closely related to SR-14,but the activity of TH-62 is unexpected given the lack of activity of the closely related TH-63–66. The beneficial effects of the free phenol group in the palmarumycin pharmacophore for Trx-1/TrxR inhibition are most strikingly demonstrated in the comparison of TH-169 and TH-223. Only the free phenol TH-169 maintains significant activity while the methyl ether TH-223 is practically inactive. The comparison between palmarumycin $CP_1$, and TH-169 also demonstrates the contribution to activity by the naphthalenediolketal; a replacement with the 1,3-dioxolane group decreases activity approximately 10 fold and, most significantly, reduces the Trx-1 selectivity from >30 to approximately 2 fold.

TABLE II $IC_{50}$ values [μM] and 50% cell growth inhibition activities [μM] of Trx-1/TrxR inhibitors.

| No. | Compound | TrxR | Trx-1/TrxR | MDA-MB-231 | MCF-7 |
|---|---|---|---|---|---|
|  | palmarumycin CP 1 | 12.0 | 0.35 | 2.4 | 1 |
|  | diepoxin | 13.5 | 4.5 | 2 | 1.5 |
| 21 | SR-1 | nd | >50 | 7.5 | 7.9 |
| 22 | SR-2 | nd | >50 | 2.9 | 1.3 |
| 23 | SR-3 | nd | >50 | 13.6 | 13.4 |
| 24 | SR-4 | nd | >50 | 9.2 | >30 |
| 25 | SR-5 | nd | >50 | 2.7 | 2.3 |
| 26 | SR-6 | nd | >50 | 4.6 | 3.9 |
| 27 | SR-7 | nd | >50 | 2.5 | 1.1 |
| 29 | SR-9 | nd | >50 | 2 | 4.6 |
| 30 | SR-10 | >50 | 23.2 | 2 | 2 |
| 31 | SR-11 | >50 | 41.8 | 2.8 | 2 |
| 32 | SR-12 | >50 | >50 | 1.4 | 1.5 |
| 33 | SR-13 | >50 | >50 | 7.3 | 8 |
| 34 | SR-14 | >50 | 23.2 | 2.7 | 2 |
|  | TH-39 | >50 | >50 | 2.2 | 0.7 |
|  | TH-40 | >50 | 4.8 | 8.2 | 7.8 |
|  | TH-44 | >50 | 13.4 | 4.7 | 4.3 |
|  | TH-48 | >50 | >50 | 9.3 | >10 |
|  | TH-49 | >50 | >50 | 8 | >10 |
|  | TH-62 | 20.1 | 10.2 | 7.8 | 5.7 |
|  | TH-63 | >50 | >50 | >10 | >10 |
|  | TH-64 | >50 | >50 | >10 | >10 |
|  | TH-65 | >50 | >50 | 4.9 | 5 |
|  | TH-66 | >50 | 42.4 | 5.2 | 5.5 |
|  | TH-126 | nd | >50 | 3.6 | 2 |
|  | TH-139 | nd | >50 | 5.3 | 4.3 |
|  | TH-140 | nd | >50 | 4.5 | 1.9 |
|  | TH-169 | 8.8 | 3.4 | 4.3 | 4.2 |
|  | TH-223 | >50 | 40.2 | 5 | 4.4 |

$IC_{50}$ values were calculated from 5 concentrations (0.1 to 50 μM) for both the Trx-1/TrxR and TrxR assays.
nd = not determined Two compounds, 24 referred to herein as SR-4 and 27 referred to herein as SR-7, were examined in greater detail as to their effects on biological activity. The proliferation of MCF-7, MDA-MB-231 and SV40 transformed mouse embryonic fibroblasts was measured by a previously described colorimetric assay (Wipf P, Jung J–K, Rodriguez S, Lazo JS Synthesis and biological evaluation of Deoxypreussomerin A and Palmarumycin CP 1 and related naphthoquinone spiroketals. Tetrahedron 57:283–296, 2001 and Vogt A, Rice RL, Settineri CE, Yokokawa F, Yokokawa S, Wipf P and Lazo JS (1998) Disruption of insulin-like growth factor-I signaling and down-regulation of Cdc2 by SC-ααδ9, a novel small molecule antisignaling agent identified in a targeted array library. J Pharmacol Exptl Therap 287:806–813.). Briefly, the inventors seeded 4,000-6,000 cells per well in microtiter plates. Cells were allowed to attach overnight and treated with vehicle or compounds for 72 h, after which the medium was replaced with serum free medium containing 0.1% 3-[4,5-dimethylthiazol-2-yl]-2,5-diphenyl tetrazolium bromide. Plates were incubated for 3 hours in the dark and total cell number was determined by spectrophotometrically at 540 nm as previously described (Vogt A, Rice RL, Settineri CE, Yokokawa F, Yokokawa S, Wipf P and Lazo JS (1998) Disruption of insulin-like growth factor-1 signaling and down-regulation of Cdc2 by SC-ααδ9, a novel small molecule antisignaling agent identified in a targeted array library. J Pharmacol Exptl Therap 287:806–813.). The growth inhibition of 1 A9, 1 A9/PTX10 and 1 A9/PTX22 cells was also measured with a slightly different colorimetric assay. Cells were maintained in RPMI 1640 medium containing 10% fetal bovine serum and the paclitaxel-resistant cells also contained 17 nM paclitaxel and 10 μM verapamil. Cells were plated (2,000/well) in 96-well plates and allowed to attach and grow for 72 hours (paclitaxel and verapamil were removed from resistant cell medium two weeks prior to this plating). They were then treated with 0.5% DMSO vehicle control or 0.08–10 μM compound. The number of cells was determined spectrophotometrically at 490 nm minus absorbance at 630 nm after exposure to 3-(4,5-dimethylthiazol-2-yl)-5-(3-carboxymethoxyphenyl)-2-(4-sulfophenyl)-2H-tetrazolium and N-methyldibenzopyurazine methyl sulfate.

Exponentially growing MCF-7 (FIG. 23, Panel A) or MDA-MB-231 (Panel B) cells were exposed to various concentrations of palmarumycin $CP_1$, diepoxin (7, SR-7 or SR-4 for 72 hours and the cell number determined using 0.1% 3-[4,5-dimethylthiazol-2-yl]-2,5-diphenyl tetrazolium bromide as described elsewhere herein. Control values were vehicle treated cells. N=8, Bars=SEM. MCF-7 cells showed similar sensitivity to the antiproliferative actions of palmarumycin $CP_1$, diepoxin a and SR-7 with an $IC_{50}$ of approximately 1–2 μM (Panel A). In contrast, the close structural analog SR-4 had considerably less antiproliferative activity against these cells with an $IC_{50}$ greater than 10 μM. Because of the potential importance of the tumor suppressor gene p53 and the estrogen receptor in controlling the cellular response to cytotoxic agents, the inventors also examined the sensitivity of MDA-MB-231 cells, which lack functional p53 and estrogen receptors. As can be appreciated by reference to FIG. 23, Panel B, MDA-MB-231 cells were equally sensitive to palmarumycin $CP_1$, diepoxin σ and SR-7. When compared to SR-7, however, SR-4 was again less active revealing the importance of the 2-furyl moiety in the C8 position of SR-7. As might be expected, these p53 and estrogen receptor deficient cells were generally less sensitive to both natural products and analogs when compared to MCF-7 cells. The differential cytotoxicity of the SR-7:SR-4 pair was confirmed when the inventors tested mouse embryonic fibroblasts transformed with SV40 large T antigen; the inventors found 3 μM SR-7, palmarumycin $CP_1$, and diepoxin σ were required to inhibit growth by 50%, while no significant inhibition was seen with 10 μM SR-4, the highest concentration tested (data not shown).

Flow cytometry analysis tsFT210 cells were seeded at 2 x $10^5$ cells/ml and maintained at 32.0° C. as previously described (Tamura K, Rice RL, Wipf P and Lazo JS (1999) Dual G1 and G2/M phase inhibition by SC-αα$\delta$9, a combinatorially derived Cdc25 phosphatase inhibitor. Oncogene 18:6989–6996, Th'ng JP, Wright PS, Hamaguchi J, Lee MG, Norbury CJ, Nurse P and Bradbury EM (1990) The FT210 cell line is a mouse G2 phase mutant with a temperature-sensitive CDC2 gene product. Cell 63:313-324.). Cell proliferation was blocked at G2 phase by incubation at 39.4° C. for 17 h. The synchronized cells were then released by re-incubating at 32.0° C. and treated immediately with 0–10 μM SR-7, 1 μM nocodazole or 100 EM SC-αα$\delta$9, respectively, to probe for G2/M arrest. Cells were treated 6 hours after G2/M release to determine G1 arrest. The inventors used 100 μM SC-αα$\delta$9 and 50 μM roscovitine as positive control compounds for G1 arrest. A final concentration of 0.5% DMSO was used for all compounds and as a negative control. For both G2/M and G1 blockage studies, treated cells were incubated at 32.0° C. for an additional 6 hours after each drug exposure, and then harvested with phosphate buffered saline at 5×$10^5$ cells/ml. The harvested cells were stained with a solution containing 50 μg/ml propidium iodide and 250 μg/ml RNase A. Flow cytometry analysis was conducted with a Becton Dickinson FACS Star (Franklin Lakes, N.J.).

When incubated at the permissive temperature of 32.0° C., tsFT210 cells had a normal cell cycle distribution (FIG. 24, Panel A); when incubated at the non-permissive temperature of 39.4° C. for 17 h, cells arrested at G2/M phase (4C), due to Cdk1 inactivation (Panel B). When G2/M arrested cells were cultured at the permissive temperature for 6 hours with DMSO vehicle alone, the inventors saw clear evidence of entry into G1 (2C) (Panel C), although a small fraction of cells remained in the G2/M phase. This G2/M retention at 4C is probably due to the extended cell cycle blockage at 39.4° C. (Osada H, Cui CB, Onose R and Hanaoka F (1997) Screening of cell cycle inhibitors from microbial metabolites by a bioassay using a mouse cdc2 mutant cell line, tsFT210. Bioorg Med Chem 5:193–203). Treatment with 1 μM nocodazole blocked cell passage through G2/M (Panel D).

To determine the effect of SR-7 on G2/M cell cycle transition, the inventors treated cells with 2.5 to 10 μM SR-7 for 6 hours after releasing cells at 32.0° C. As indicated in Panels E–H, SR-7 caused a concentration-dependent arrest in the G2/M phase, with obvious blockage even with 2.5 μM SR-7. The G2/M inhibition was similar to that seen with the previously reported and structurally unrelated compound SC-αα$\delta$9 (Panel I). SC-αα$\delta$9 is an inhibitor of the Cdc25 family of phosphatases that controls cell cycle checkpoints (Rice RL, Rusnak JM, Yokokawa F, Yokokawa S, Messner DJ, Boynton AL, Wipf P and Lazo JS (1997) A targeted library of small molecule, tyrosine and dual specificity phosphatase inhibitors derived from a rational core design and random side chain variation. Biochemistry 36:15965–15974).

The inventors examined G1 transition in tsFT210 cells after SR-7 treatment. tsFT210 cells were cultured at the permissive temperature of 32.0° C. (FIG. 25, Panel A) and then incubated for 17 hours at the non-permissive temperature of 39.4° C. (Panel B). Cells were released from the G2/M block by incubation at 32.0° C. for 6 hours (Panel C), and then incubated for an additional 6 hours in the presence of various agents. These were: DMSO vehicle (Panel D), 50 μM roscovitine (Panel E), 5 μM SR-7 (Panel F), 10 μM SR-7 (Panel G), or 100 μM SC-αα$\delta$9 (Panel H). Fluorescence corresponding to 2C and 4C DNA contents is represented by vertical bars. These results were replicated in a second independent experiment. Cells that were treated with the DMSO vehicle passed through G1 phase as expected and produced the predicted broad S phase peak between diploid (2C) and tetraploid (4C) states (D), while cells exposed continuously to 50 μM roscovitine were blocked and did not pass through G1 (Panel E). As illustrated in Panels F and G, cells treated with 5 or 10 μM SR-7 were not delayed at G1. As expected from previous studies (Tamura K, Southwick EC, Kerns J, Rosi K, Carr BI, Wilcox C and Lazo JS (2000) Cdc25 inhibition and cell cycle arrest by a synthetic thioalkyl vitamin K analogue. Cancer Res 60:1317–1325.), the dual phase-specific inhibitor SC-αα$\delta$9 caused a prominent G1 block and also prevented cells that were at the G2/M interphase from progressing, which resulted in two prominent cell cycle peaks (Panel H).

Western blotting and Cdk1 assays.

tsFT210 cells were harvested using the same procedure for cell synchronizing and drug exposure as described above for the G2/M flow cytometric analysis. The protein lysates were analyzed by Western blotting for Cdk1 as described previously (Tamura K, Southwick EC, Kerns J, Rosi K, Carr BI, Wilcox C and Lazo JS (2000) Cdc25 inhibition and cell cycle arrest by a synthetic thioalkyl vitamin K analogue. Cancer Res 60:1317–1325.). The inventors used Cdk1 isolated from human MCF-7 cells to assay for in vitro inhibition of enzyme activity because of available antibodies and convenience. Asynchronous cells grown at 37° C. in 5% $CO_2$ in DMEM containing 10% fetal bovine serum were treated with lysis buffer and harvested as previously described (Vogt A, Wang AS, Johnson CS, Fabisiak JP, Wipf P and Lazo JS (2000) In vivo antitumor activity and induction of insulin-like growth factor-1 resistant apoptosis by SC-αα$\delta$9. J Pharmacol Exptl Therap 292:530–537.). Cdk1 kinase activity assay was performed as previously described (Yu L, Orlandi L, Wang P, Orr MS, Senderowicz AM, Sausville EA, Silvestrini R, Watanabe N, Piwnica-Worms H, O° Connor PM (1998) UCN-01 arogates G2 arrest through a Cdc2-dependent pathway that is associated with inactivation of the WeelHu kinase and activation of the Cdc25C phosphatase. J Biol Chem 273: 33455–33464.). Briefly, 2 mg of the protein lysates were incubated with antiCdk1 antibody agarose conjugate for 2 hours at 4 °C. The immunoprecipitates were treated in vitro with DMSO vehicle, 300 nM flavopiridol or 10 iM SR-7 for 20 min at 30° C. The treated immunoprecipitates were re-incubated in 20 $\mu$l of kinase reaction buffer (Yu L, Orlandi L, Wang P, Orr MS, Senderowicz AM, Sausville EA, Silvestrini R, Watanabe N, Piwnica-Worms H, O'Connor PM (1998) UCN-01 arogates G2 arrest through a Cdc2-dependent pathway that is associated with inactivation of the WeelHu kinase and activation of the Cdc25C phosphatase. J Biol Chem 273: 33455–33464.) for an additional 20 min at 30° C. with 3 $\mu$g of histone H1, 20 mM Tris-HCl, 10 mM MgCl$_2$, 5 $\mu$M cold ATP and 10 $\mu$Ci of [$\gamma$-$^{32}$P]ATP. Histone H1 was separated from other proteins by SDS-PAGE and analyzed for incorporation of radioactive phosphate with a Molecular Dynamics STORM 860 PhosphoImager (Sunnyvale, CA).

The major controlling molecule for G2/M transition is the cyclin dependent kinase, Cdk1, whose cellular activity is tightly regulated by phosphorylation (Pines J (1999) Four-dimensional control of the cell cycle. Nature Cell Biol 1:E73–79., Hunter T and Pines J (1994) Cyclins and cancer II: cyclin D and CDK inhibitors come of age. Cell 79:573–582). Therefore, the inventors performed Western blotting on tsFT210 cell extracts to determine the Cdk1 phosphorylation level in the presence or absence of SR-7. G2/M synchronous tsFT210 cells were treated with vehicle or various compounds and permitted to re-enter the cell cycle by culturing at 32.0° C. The inventors isolated protein lysates from cells that were not incubated (0 h) or from cells incubated for 2–6 hours at the permissive temperature in the presence of a compound or vehicle. The protein lysates were analyzed by Western blotting for Cdk1 content and phosphorylation status as described elsewhere herein.

FIG. 26 depicts the results of the Cdk1 assay in which DMSO control, 0–6 hours is shown in lanes 1–4. Nocodazole, 1 $\mu$M for 6 hours in lane 5, SR-7, 10 and 20 $\mu$M for 6 hours in lanes 6 and 7 and, SC-$\alpha\alpha\delta$9, 50 $\mu$M for 6 hours in lane 8. These results were confirmed in a second independent experiment. Similar to previous observations, approximately 50% of Cdk1 was in the mitotic-inactive hyperphosphorylated form as reflected by a slower migrating Cdk1 (lane 1). The phosphorylation of Cdk1 decreased gradually after cells were released from G2/M block, and most of the Cdkl was dephosphorylated and, thus activated, 6 hours after G2/M release, even in the presence of the DMSO vehicle (lanes 2–4). When the inventors incubated cells with 1 $\mu$M nocodazole, which caused a G2/M arrest, no hyperphosphorylation of Cdk1 was seen, consistent with its proposed inhibitory activity after Cdk1 activation (lane 5). Similarly, Cdk1 was completely dephosphorylated in the presence of either 10 or 20 $\mu$M SR-7 (lanes 6 and 7). In contrast, treatment with 100 IM SC-$\alpha\alpha\delta$9, which also causes G2/M block (Tamura K, Rice RL, Wipf P and Lazo JS (1999) Dual G1 and G2/M phase inhibition by SC-$\alpha\alpha\delta$9, a combinatorially derived Cdc25 phosphatase inhibitor. Oncogene 18:6989–6996), yielded a hyperphosphorylated Cdk1 (lane 8). In vitro studies confirmed that SR-7 and SR-4 at 30 $\mu$M caused no inhibition of recombinant Cdc25, VHR or PTPIB activity; even at 100 MM the inventors found #16% inhibition (data not shown).

The inventors also examined the ability of SR-7 to directly inhibit Cdk1 kinase activity. Lysates from asynchronous MCF-7 cells were immunoprecipitated with anti Cdk1 antibody coupled to agarose and the resulting immunoprecipitate treated with DMSO vehicle, 300 nM flavopiridol or 30 $\mu$M SR-7 for 20 min. The resulting immunocomplexes were tested for their ability to phosphorylate histone H1 using [$\gamma$-$^{32}$P]ATP. FIG. 27, Panel A shows the phosphorylation of histone H1. Panel B shows the total Cdk1 protein level as measured with an antiCdk1 antibody. Panel C shows the quantification of the intensity of histone H1 phosphorylation normalized to the total Cdk1 amount.

Tubulin polymerization

Tubulin without microtubule-associated proteins was isolated from fresh bovine brains (Hamel E and Lin CM (1984). Separation of active tubulin and microtubule-associated proteins by ultracentrifugation and isolation of a component causing the formation of microtubule bundles. Biochemistry 23:4173–4184). Inhibition of assembly reactions was carried out as described previously (Verdier-Pinard P, Lai J-Y, Yoo H-D, Yu J, Marquez B, Nagle DG, Nambu M, White JD, Falck JR, Gerwick WH, Day BW and Hamel E (1998) Structure-activity analysis of the interaction of curacin A, the potent colchicine site antimitotic agent, with tubulin and effects of analogs on the growth of MCF-7 breast cancer cells. Mol Pharmacol 53:62–76.).

The inventors examined the ability of SR-7 to alter tubulin polymerization or depolymerization in vitro. FIG. 28, Panel A. Compounds (predissolved in DMSO) were preincubated with tubulin containing monosodium glutamate at 30 °C. for 15 min. Samples were cooled to 0 °C. and GTP was added. Samples were placed in a temperature-controlled multi-cuvette holder of a spectrophotometer held at 0 °C. Baselines were established and temperature was rapidly raised to 30 °C. Turbidity development in the cuvettes was measured at 350 nm. FIG. 28, Panel B. Compounds were added to the tubulin plus monosodium glutamate mixture at 0 °C., placed in the spectrophotometer and temperature was raised to 30 °C. Addition of 0.4 mM GTP to isolated bovine brain tubulin produced robust polymerization that began to plateau approximately 20 min after microtubule assembly commenced (Panel A). Inclusion of 5 $\mu$M curacin A completely inhibited GTP-induced tubulin assembly while 1 $\mu$M curacin A caused a 50% inhibition. In contrast, SR-7 even at 40 $\mu$M caused only moderate inhibition of tubulin assembly as can be seen by reference to Panel A.

Inhibition of [$^3$H] colchicine binding

Using methods described previously (Verdier-Pinard P, Lai J-Y, Yoo H-D, Yu J, Marquez B, Nagle DG, Nambu M, White JD, Falck JR, Gerwick WH, Day BW and Hamel E (1998) Structure-activity analysis of the interaction of curacin A, the potent colchicine site antimitotic agent, with tubulin and effects of analogs on the growth of MCF-7 breast cancer cells. Mol Phannacol 53:62–76.). 5 $\mu$M [$^3$H] colchicine was incubated with either 5% DMSO vehicle or compound (5 or 50 $\mu$M) at 37° C. for 15 min with 1 $\mu$M tubulin in the presence of 1 M monosodium glutamate, 0.1 M glucose-1-phosphate, 1 mM MgCl$_2$, 1 mM GTP and 0.5 mg/ml bovine serum albumin. The solutions were filtered through two stacks of DEAE-cellulose filters and the radioactivity in the filtrate was determined by liquid scintillation spectrometry. Each series of determinations included positive controls of 5 and 50 $\mu$M curacin A. The inventors found no evidence that SR-7 could bind to the colchicine site of tubulin. As indicated in Table III, even at 50 $\mu$M SR-7 failed to significantly inhibit colchicine binding while the positive control, curacin A, caused almost 90% inhibition at 5 $\mu$M. Thus, the inventors concluded SR-7 did not compete for the most common small molecule target on tubulin, the colchicine binding site. The inventors propose that SR-7 may act at another site such as the previously characterized vinca alkaloid site.

TABLE III

Percent inhibition of [$^3$H]colchicine binding to bovine brain tubulin.

| COMPOUND | PERCENT INHIBITION | |
|---|---|---|
| | 5 μM | 50 μM |
| SR-7 | 1.5 ± 0.5 | 19.6 ± 4.5 |
| Curacin A | 89.8 ± 0.6% | 97.3 ± 3.1 |

Mean ± SEM. N = 9

Bcl-2 phosphorylation

Attempts to determine the phosphorylation status of Bcl-2 in tsFT210 cells using two different antibodies were unsuccessful due to the antibodies' inability to detect mouse Bcl-2 or the lack of specificity. Therefore, phosphorylated and non-phosphorylated Bcl-2 was detected in lysates from human MCF-7 cells (American Type Culture Collection, Manassas, Va.) treated with microtubule perturbing agents. Equal amounts of protein were separated by electrophoresis on 15% SDS-PAGE followed by immunoblotting with an antihuman Bcl-2 antibody (sc-509, Santa Cruz Biotechnology). Positive antibody reactions were visualized using peroxidase-conjugated secondary antibodies (Jackson ImmunoResearch, West Grove, Pa.) and an enhanced chemiluminescence detection system (Renaissance, NEN, Boston, Mass.) according to manufacturer's instructions.

All known microtubule disrupting compounds cause hyperphosphorylation of the antiapoptotic protein Bcl-2 (Haldar S, Jena N and Croce CM (1995) Inactivation of bcl-2 by phospliorylation. Proc Natl Acad Sci USA 92:4507–4511 and Basu A and Haldar S (1998) Microtubule-damaging drugs trigger bcl2 phosphorylation-requirement of phosphorylation on both serine-70 and serine-87 residues of bcl2 protein. Intl J Oncol 13:659–664). Therefore, the phosphorylation status of Bcl-2 in cells treated with various compounds including SR-7 was examined and the results are illustrated in FIG. 29. Proteins from lysates of MCF-7 cells treated with 0.5 μM paclitaxel, 1 μM nocodozole, 1 μM vincristine and, 3 or 10 μM SR-7 were separated by electrophoresis on 15% SDS-PAGE followed by immunoblotting with an antibody to Bcl-2. The phosphorylated form of Bcl-2 (P) appeared as the upper bands and the underphosphorylated form (U) was the lower band. These results were confirmed in a second independent experiment. Although paclitaxel, nocodazole and, vincristine caused prominent phosphorylation of Bcl-2, SR-7 at either 3 or 10 μM failed to generate significant hyperphosphorylated Bcl-2. These results strongly suggested SR-7 did not directly disrupt tubulin in whole cells.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

We claim:

1. A compound of the structural formula

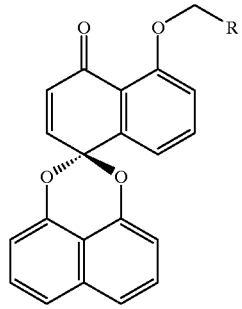

wherein r is a member selected from the group consisting of (e)-HC=CHPh, (e)-hc=CHMe, n-C$_5$H$_{11}$, (e)-CH$_2$HC=CHEt, (m)-MeOPH, benzonitrile, 2-furyl, (E,E)-HC=C(ME)CH$_2$CH$_2$CH=CMe$_2$, 3-furyl, 2-pyridyl, 3-pyridyl, 4-pyridyl, and HC=CH$_2$.

2. A compound of the structural formula

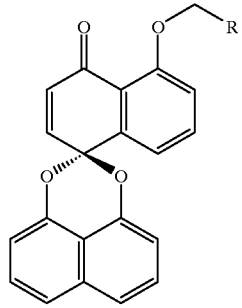

wherein R is a member selected from the group consisting of (p)-MeOPh, C(Me)=CH$_2$, C==H, (p)-BrPh, (p)-ClPh, 2-furyl(5-(p)-BrPh), 2-furyl(5-(o)-ClPh), 2-furyl(5-(m)-ClPh), 2-furyl(5-(o)-CF$_3$Ph), 2-furyl(5-(m)-CF$_3$Ph), HC=CMe$_2$, (E)-C(Me)=CHMe, and (Z)C(Me)=-CHMe.

* * * * *

UNITED STATES PATENT AND TRADEMARK OFFICE
CERTIFICATE OF CORRECTION

PATENT NO.   : 6,673,937 B2
DATED        : January 6, 2004
INVENTOR(S)  : Lazo et al.

It is certified that error appears in the above-identified patent and that said Letters Patent is hereby corrected as shown below:

Title page, Item [54] and Column 1, line 1,
Title, please delete "SYNTHESES" and insert therefore -- SYNTHESIS --.

Column 2,
Line 56, delete "C6" and insert therefore -- C16 --.

Column 3,
Line 26, delete "Miler" and insert therefore -- Miller --.
Line 46, delete "IC 50" and insert therefore -- $IC_{50}$ --.
Line 47, delete "GI 50" and insert therefore -- $GI_{50}$ --.

Column 4,
Line 3, delete "2 '-naphtho[" and insert therefore -- 2'-naphtho[ --.
Line 46, delete "CP1" and insert therefore -- $CP_1$ --.
Line 64, delete "-spiro-2'''-dioxolane" and insert therefore -- spiro-2"-dioxolane --.

Column 5,
Line 28, delete "SC-ααδuoa9" and insert therefore -- SC-ααδ9 --.

Column 6,
Line 11, delete "(1 OmCi/mmol)" and insert therefore -- (10mCi/mmol) --.
Line 42, delete "famesyl" and insert therefore -- famesyl --.
Line 60, delete "Florke" and insert therefore -- Flörke --.

Column 8,
Line 3, delete "Schlingmann" and insert therefore -- Schlingmann --.
Line 5, delete "CS" and insert therefore -- CJ --.
Line 8, delete "Beman" and insert therefore -- Beman --.
Line 17, delete "*Aiztibiot*" and insert therefore -- *Antibiot* --.
Line 46, delete "1," and insert therefore -- I, --.
Line 47, delete "$C_1$," and insert therefore -- $C_{11}$ --.
Line 56, delete "by" and insert therefore -- be --.
Line 56, delete "be" and insert therefore -- by --.

Column 9,
Lines 19 and 24, delete "Ph1(OAc)$_2$" and insert therefore -- PhI(OAc)$_2$ --.
Line 35, delete "adsorbed" and insert therefore -- absorbed --.

UNITED STATES PATENT AND TRADEMARK OFFICE
CERTIFICATE OF CORRECTION

PATENT NO. : 6,673,937 B2
DATED : January 6, 2004
INVENTOR(S) : Lazo et al.

It is certified that error appears in the above-identified patent and that said Letters Patent is hereby corrected as shown below:

Column 10,
Line 6, delete "is olation" and insert therefore -- isolation --.
Line 47, delete "10067".
Line 52, delete "$Cu_2O$" and insert therefore -- $Cu_2O$ --.

Column 11,
Line 11, delete "(M+," and insert therefore -- ($M^+$, --.
Line 30, delete "2,70" and insert therefore -- 2.70 --.
Line 31, delete "2.06 p," and insert therefore -- 2.06 (p, --.
Line 34, delete "(M+," and insert therefore -- (M', --.
Line 50, delete "735 cm " and insert therefore -- 735 cm-I --.
Line 59, delete "(M+," and insert therefore -- ($M^+$, --.
Line 65, delete "nunol" and insert therefore -- mmol --.

Column 12,
Line 7, delete "THE/MeOH" and insert therefore -- THF/MeOH --.
Line 16, delete "3057." and insert therefore -- 3057, --.
Line 18, delete "759 $cm^{+1}$" and insert therefore -- 759 $Cm^{-1}$ --.
Line 26, delete "364(M+," and insert therefore -- 364($M^+$, --.
Line 30, delete "[1",8"" and insert therefore -- [1",8"-de][1',3'] --.
Line 31, delete "',3']".
Line 50, delete "(E1)", and insert therefore -- (EI) --.
Line 51, delete "(M+," and insert therefore -- ($M^+$, --.
Line 58, delete "nmmol)" and insert therefore -- mmol) --.
Line 58, delete "nmL)" and insert therefore -- mL) --.

Column 13,
Line 1, delete "fmie" and insert therefore -- fine --.
Line 2, delete "Ph1" and insert therefore -- PhI --.
Line 6, delete "nmL" and insert therefore -- mL --.
Line 6, delete "Na2SO4" and insert therefore -- $Na_2SO_4$ --.
Line 7, delete "SiO2" and insert therefore -- $SiO_2$ --.
Line 11, delete "$^1$HNMR" and insert therefore -- $^1$H MNR --.
Line 17, delete "E1" and insert therefore -- EI --.
Line 17, delete "mn/z" and insert therefore -- m/z --.
Line 18, delete "M+" and insert therefore – $M^+$ --.
Line 21, delete "E1" and insert therefore -- EI --.
Line 24, delete "CP,)" and insert therefore -- $CP^1$) --.
Line 32, delete "mnmol" and insert therefore -- mmol --.
Line 32, delete "$P_2O_5$" and insert therefore -- $P_2O_5$ --.

UNITED STATES PATENT AND TRADEMARK OFFICE
CERTIFICATE OF CORRECTION

PATENT NO. : 6,673,937 B2
DATED : January 6, 2004
INVENTOR(S) : Lazo et al.

It is certified that error appears in the above-identified patent and that said Letters Patent is hereby corrected as shown below:

Column 13 (cont'd),
Line 35, delete "mnL" and insert therefore -- mL --.
Line 37, delete "CPI" and insert therefore -- $CP_1$ --.
Line 40, delete "$cm^1$" and insert therefore -- $cm^{-1}$ --.
Line 40, delete "'HNMR " and insert therefore -- $^1$H NMR --.
Line 40, before "12.17", insert -- δ --.
Line 46, delete "E1" and insert therefore -- EI --.
Line 46, delete "M+" and insert therefore -- $M^+$ --.
Line 48, delete "E1" and insert therefore -- EI --.
Lines 49 and 51, delete "+" and insert therefore -- ± --.
Line 53, delete "gL" and insert therefore -- μL --.
Line 59, after "47%" delete -- /o --.
Line 64, delete "niL" and insert therefore -- mL --.

Column 14,
Line 1, delete "$P_2O_5$" and insert therefore -- $P_2O_5$ --.
Line 6, delete "+" and insert therefore -- ± --.
Line 9, delete "$^1$HNMR " and insert therefore -- $^1$H NMR --.
Line 17, delete "E1" and insert therefore -- EI --.
Lines 24, 37 and 47, delete "CPI" and insert therefore -- $CP_1$ --.
Line 26, delete "laL" and insert therefore -- μL --.
Line 39, delete "4 )" and insert therefore -- 4 H) --.
Line 49, before "μL" delete -- p --.
Line 49, delete "mnmol)" and insert therefore -- mmol) --.
Line 50, delete "liL" and insert therefore -- μL --.
Line 66, after "50%" delete -- /o --.

Column 15,
Line 23, delete "niL" and insert therefore -- μL --.
Line 32, delete "CP," and insert therefore -- $CP_1$ --.
Line 34, delete "nmmol" and insert therefore -- mmol -- in both occurrences.
Line 47, after "2.8" delete -- , --.
Line 59, delete "naphtol" and insert therefore -- naphto --.
Line 62, after "5.6" delete -- , --.

Column 16,
Line 5, delete "[1',8'-de]" and insert therefore -- [1",8"-de] --.

UNITED STATES PATENT AND TRADEMARK OFFICE
CERTIFICATE OF CORRECTION

PATENT NO.    : 6,673,937 B2
DATED         : January 6, 2004
INVENTOR(S)   : Lazo et al.

It is certified that error appears in the above-identified patent and that said Letters Patent is hereby corrected as shown below:

Column 17,
Line 5, delete "dihydronaphthalene4" and insert therefore -- dihydronaphthalene-4 --.
Line 20, delete "(s,3 H);$^{13}$;" and insert therefore -- (s,3 H);$^{13}$ --.
Line 28, delete "TH-169.-" and insert therefore -- TH-169: --.
Line 35, delete "E1" and insert therefore -- EI --.
Lines 43 and 44, delete "1H" and insert therefore -- 1 H --.
Line 66, delete "a" and insert therefore -- σ --.

Column 18,
Line 18, delete "mamnmary" and insert therefore -- mammary --.
Line 36, after "30" delete -- , --.

Column 19,
Line 30, delete "affinity" and insert therefore -- affimity --.
Line 50, delete "Trx-1/TrxR" and insert therefore -- Trx--I/TrxR --.

Column 20,
Line 33, delete "factor-I" and insert therefore -- factor-1 --.
Line 66, delete "diepoxin (7" and insert therefore -- diepoxin σ --.

Column 21,
Line 5, delete "diepoxin a" and insert therefore -- diepoxin D --.
Line 31, delete "GI" and insert therefore -- G1 --.
Line 41, delete "EM" and insert therefore -- $\mu$M --.

Column 22,
Lines 26 and 34, after "50" delete -- , --.

Column 23,
Line 6, after "10" delete -- i -- and insert therefore -- μ --.
Line 40, after "20" delete -- , --.
Line 41, after "50" delete -- , --.
Line 56, delete "IM" and insert therefore -- $\mu$M --.
Line 63, delete "MM" and insert therefore -- $\mu$M --.

Column 24,
Line 40, after "5" delete -- , --.
Line 52, delete "Phannacol" and insert therefore -- Pharmocol --.
Line 52, after "5" delete -- , --.

UNITED STATES PATENT AND TRADEMARK OFFICE
CERTIFICATE OF CORRECTION

PATENT NO.    : 6,673,937 B2
DATED         : January 6, 2004
INVENTOR(S)   : Lazo et al.

It is certified that error appears in the above-identified patent and that said Letters Patent is hereby corrected as shown below:

Column 25,
Line 42, after "1" delete -- , --.

Column 26,
Line 25, delete "r" and insert therefore -- R --.
Line 26, delete "(e)-HC=CHPh" and insert therefore -- (E)-HC=CHPh --.
Line 26, delete "(e)-hc=CHMe, n-$C_5H_{11}$" and insert therefore -- (E)-HC=CHMe, n-$C_5H_{11}$ --.
Line 26, delete "(e)-$CH_2$HC=CHEt" and insert therefore -- (E)-$CH_2$HC=CHEt --.
Line 27, delete "OPH" and insert therefore -- OPh --.
Line 27, delete "ME" and insert therefore -- Me --.
Line 28, delete "$_3$-furyl" and insert therefore -- 3-furyl --.
Line 46, delete "C=H" and insert therefore -- C=CH --.

Signed and Sealed this

Fifteenth Day of March, 2005

JON W. DUDAS
*Director of the United States Patent and Trademark Office*

UNITED STATES PATENT AND TRADEMARK OFFICE
CERTIFICATE OF CORRECTION

PATENT NO.    : 6,673,937 B2
DATED         : January 6, 2004
INVENTOR(S)   : Lazo et al.

It is certified that error appears in the above-identified patent and that said Letters Patent is hereby corrected as shown below:

Title page, Item [54] and Column 1, line 1,
Title, please delete "SYNTHESES" and insert therefore -- SYNTHESIS --.

Column 2,
Line 56, delete "C6" and insert therefore -- C16 --.

Column 3,
Line 26, delete "Miler" and insert therefore -- Miller --.
Line 46, delete "IC 50" and insert therefore -- $IC_{50}$ --.
Line 47, delete "GI 50" and insert therefore -- $GI_{50}$ --.

Column 4,
Line 3, delete "2 '-naphtho[" and insert therefore -- 2'-naphtho[ --.
Line 46, delete "CP1" and insert therefore -- $CP_1$ --.
Line 64, delete "-spiro-2'''-dioxolane" and insert therefore -- spiro-2''-dioxolane --.

Column 5,
Line 28, delete "SC-ααδuoa9" and insert therefore -- SC-ααδ9 --.

Column 6,
Line 11, delete "(1 OmCi/mmol)" and insert therefore -- (10mCi/mmol) --.
Line 42, delete "famesyl" and insert therefore -- farnesyl --.
Line 60, delete "Florke" and insert therefore -- Flörke --.

Column 8,
Line 3, delete "Schlingmann" and insert therefore -- Schlingmann --.
Line 5, delete "CS" and insert therefore -- CJ --.
Line 8, delete "Beman" and insert therefore -- Beman --.
Line 17, delete "*Aiztibiot*" and insert therefore -- *Antibiot* --.
Line 46, delete "1," and insert therefore -- I, --.
Line 47, delete "$C_1$," and insert therefore -- $C_{11}$ --.
Line 56, delete "by" and insert therefore -- be --.
Line 56, delete "be" and insert therefore -- by --.

Column 9,
Lines 19 and 24, delete "Ph1(OAc)$_2$" and insert therefore -- PhI(OAc)$_2$ --.
Line 35, delete "adsorbed" and insert therefore -- absorbed --.

UNITED STATES PATENT AND TRADEMARK OFFICE
CERTIFICATE OF CORRECTION

PATENT NO. : 6,673,937 B2
DATED : January 6, 2004
INVENTOR(S) : Lazo et al.

It is certified that error appears in the above-identified patent and that said Letters Patent is hereby corrected as shown below:

Column 10,
Line 6, delete "is olation" and insert therefore -- isolation --.
Line 47, delete "10067".
Line 52, delete "Cu$_2$O" and insert therefore -- Cu$_2$O --.

Column 11,
Line 11, delete "(M+," and insert therefore -- (M$^+$, --.
Line 30, delete "2,70" and insert therefore -- 2.70 --.
Line 31, delete "2.06 p," and insert therefore -- 2.06 (p, --.
Line 34, delete "(M+," and insert therefore -- (M$^+$, --.
Line 50, delete "735 cm " and insert therefore -- 735 cm$^{-1}$ --.
Line 59, delete "(M+," and insert therefore -- (M$^+$, --.
Line 65, delete "nunol" and insert therefore -- mmol --.

Column 12,
Line 7, delete "THE/MeOH" and insert therefore -- THF/MeOH --.
Line 16, delete "3057." and insert therefore -- 3057, --.
Line 18, delete "759 cm$^{+1}$" and insert therefore -- 759 cm$^{-1}$ --.
Line 26, delete "364(M+," and insert therefore -- 364(M$^+$, --.
Line 30, delete "[1",8"" and insert therefore -- [1",8"-de][1',3'] --.
Line 31, delete "',3']".
Line 50, delete "(E1)", and insert therefore -- (EI) --.
Line 51, delete "(M+," and insert therefore -- (M$^+$, --.
Line 58, delete "nmmol)" and insert therefore -- mmol) --.
Line 58, delete "nmL)" and insert therefore -- mL) --.

Column 13,
Line 1, delete "fmie" and insert therefore -- fine --.
Line 2, delete "Ph1" and insert therefore -- PhI --.
Line 6, delete "nmL" and insert therefore -- mL --.
Line 6, delete "Na2SO4" and insert therefore -- Na$_2$SO$_4$ --.
Line 7, delete "SiO2" and insert therefore -- SiO$_2$ --.
Line 11, delete "$^1$HNMR" and insert therefore -- $^1$H MNR --.
Line 17, delete "E1" and insert therefore -- EI --.
Line 17, delete "mn/z" and insert therefore -- m/z --.
Line 18, delete "M+" and insert therefore – M$^+$ --.
Line 21, delete "E1" and insert therefore -- EI --.
Line 24, delete "CP,)" and insert therefore – CP$^1$) --.
Line 32, delete "mnmol" and insert therefore -- mmol --.
Line 32, delete "P$_2$0$_5$" and insert therefore -- P$_2$O$_5$ --.

UNITED STATES PATENT AND TRADEMARK OFFICE
CERTIFICATE OF CORRECTION

PATENT NO. : 6,673,937 B2
DATED : January 6, 2004
INVENTOR(S) : Lazo et al.

It is certified that error appears in the above-identified patent and that said Letters Patent is hereby corrected as shown below:

Column 13 (cont'd),
Line 35, delete "mnL" and insert therefore -- mL --.
Line 37, delete "CPI" and insert therefore -- $CP_1$ --.
Line 40, delete "$cm^1$" and insert therefore -- $cm^{-1}$ --.
Line 40, delete "'HNMR " and insert therefore -- $^1H$ NMR --.
Line 40, before "12.17", insert -- δ --.
Line 46, delete "E1" and insert therefore -- EI --.
Line 46, delete "M+" and insert therefore -- $M^+$ --.
Line 48, delete "E1" and insert therefore -- EI --.
Lines 49 and 51, delete "+" and insert therefore -- ± --.
Line 53, delete "gL" and insert therefore -- $\mu$L --.
Line 59, after "47%" delete -- /o --.
Line 64, delete "niL" and insert therefore -- mL --.

Column 14,
Line 1, delete "$P_2O_5$" and insert therefore -- $P_2O_5$ --.
Line 6, delete "+" and insert therefore -- ± --.
Line 9, delete "$^1$HNMR " and insert therefore -- $^1H$ NMR --.
Line 17, delete "E1" and insert therefore -- EI --.
Lines 24, 37 and 47, delete "CPI" and insert therefore – $CP_1$ --.
Line 26, delete "laL" and insert therefore -- $\mu$L --.
Line 39, delete "4 )" and insert therefore -- 4 H) --.
Line 49, before "$\mu$L" delete -- p --.
Line 49, delete "mnmol)" and insert therefore -- mmol) --.
Line 50, delete "liL" and insert therefore -- $\mu$L --.
Line 66, after "50%" delete -- /o --.

Column 15,
Line 23, delete "niL" and insert therefore -- $\mu$L --.
Line 32, delete "CP," and insert therefore -- $CP_1$ --.
Line 34, delete "nmmol" and insert therefore -- mmol -- in both occurrences.
Line 47, after "2.8" delete -- , --.
Line 59, delete "naphtol" and insert therefore -- naphto --.
Line 62, after "5.6" delete -- , --.

Column 16,
Line 5, delete "[1',8'-de]" and insert therefore -- [1",8"-de] --.

UNITED STATES PATENT AND TRADEMARK OFFICE
CERTIFICATE OF CORRECTION

PATENT NO. : 6,673,937 B2
DATED : January 6, 2004
INVENTOR(S) : Lazo et al.

It is certified that error appears in the above-identified patent and that said Letters Patent is hereby corrected as shown below:

Column 17,
Line 5, delete "dihydronaphthalene4" and insert therefore -- dihydronaphthalene-4 --.
Line 20, delete "(s,3 H);$^{13}$;" and insert therefore -- (s,3 H);$^{13}$ --.
Line 28, delete "TH-169.-" and insert therefore -- TH-169: --.
Line 35, delete "E1" and insert therefore -- EI --.
Lines 43 and 44, delete "1H" and insert therefore -- 1 H --.
Line 66, delete "a" and insert therefore -- σ --.

Column 18,
Line 18, delete "mamnmary" and insert therefore -- mammary --.
Line 36, after "30" delete -- , --.

Column 19,
Line 30, delete "affinity" and insert therefore -- affimity --.
Line 50, delete "Trx-1/TrxR" and insert therefore -- Trx--I/TrxR --.

Column 20,
Line 33, delete "factor-I" and insert therefore -- factor-1 --.
Line 66, delete "diepoxin (7" and insert therefore -- diepoxin σ --.

Column 21,
Line 5, delete "diepoxin a" and insert therefore -- diepoxin σ --.
Line 31, delete "GI" and insert therefore -- G1 --.
Line 41, delete "EM" and insert therefore -- $\mu$M --.

Column 22,
Lines 26 and 34, after "50" delete -- , --.

Column 23,
Line 6, after "10" delete -- i -- and insert therefore -- μ --.
Line 40, after "20" delete -- , --.
Line 41, after "50" delete -- , --.
Line 56, delete "IM" and insert therefore -- $\mu$M --.
Line 63, delete "MM" and insert therefore -- $\mu$M --.

Column 24,
Line 40, after "5" delete -- , --.
Line 52, delete "Phannacol" and insert therefore -- Pharmocol --.
Line 52, after "5" delete -- , --.

UNITED STATES PATENT AND TRADEMARK OFFICE
CERTIFICATE OF CORRECTION

PATENT NO. : 6,673,937 B2
DATED : January 6, 2004
INVENTOR(S) : Lazo et al.

It is certified that error appears in the above-identified patent and that said Letters Patent is hereby corrected as shown below:

Column 25,
Line 42, after "1" delete -- , --.

Column 26,
Line 25, delete "r" and insert therefore -- R --.
Line 26, delete "(e)-HC=CHPh" and insert therefore -- (E)-HC=CHPh --.
Line 26, delete "(e)-hc=CHMe, n-C$_5$H$_{11}$" and insert therefore -- (E)-HC=CHMe, n-C$_5$H$_{11}$ --.
Line 26, delete "(e)-CH$_2$HC=CHEt" and insert therefore -- (E)-CH$_2$HC=CHEt --.
Line 27, delete "OPH" and insert therefore -- OPh --.
Line 27, delete "ME" and insert therefore -- Me --.
Line 28, delete "$_3$-furyl" and insert therefore -- 3-furyl --.
Line 46, delete "C=H" and insert therefore -- C=CH --.

This certificate supersedes Certificate of Correction issued March 15, 2005.

Signed and Sealed this

Sixth Day of September, 2005

JON W. DUDAS
*Director of the United States Patent and Trademark Office*